(12) United States Patent
Von Oepen et al.

(10) Patent No.: US 7,785,318 B2
(45) Date of Patent: Aug. 31, 2010

(54) CATHETER HAVING PLURALITY OF STIFFENING MEMBERS

(75) Inventors: Randolf Von Oepen, Los Altos Hills, CA (US); Axel Grandt, Strassberg (DE); Thomas Rieth, Hirrlingen (DE)

(73) Assignee: Abbott Laboratories, Abbott Park, IL (US)

(*) Notice: Subject to any disclaimer, the term of this patent is extended or adjusted under 35 U.S.C. 154(b) by 1018 days.

(21) Appl. No.: 11/439,810

(22) Filed: May 23, 2006

(65) Prior Publication Data

US 2007/0016165 A1 Jan. 18, 2007

Related U.S. Application Data

(63) Continuation of application No. 11/136,640, filed on May 23, 2005, now Pat. No. 7,625,353.

(60) Provisional application No. 60/575,643, filed on May 27, 2004, provisional application No. 60/684,135, filed on May 23, 2005, provisional application No. 60/654,022, filed on Feb. 17, 2005.

(51) Int. Cl.
*A61M 25/00* (2006.01)

(52) U.S. Cl. .................................... 604/525

(58) Field of Classification Search ............ 604/103.04, 604/103.09, 509, 528, 264, 523, 524, 525
See application file for complete search history.

(56) References Cited

U.S. PATENT DOCUMENTS

| | | | |
|---|---|---|---|
| 4,490,421 A | 12/1984 | Levy | |
| 4,563,181 A | 1/1986 | Wijayarathna et al. | |
| 4,721,115 A | 1/1988 | Owens | |
| 4,748,982 A | 6/1988 | Horzewski et al. | |
| 4,762,129 A | 8/1988 | Bonzel | |
| 4,771,777 A | 9/1988 | Horzewski et al. | |
| RE32,983 E | 7/1989 | Levy | |
| 4,877,031 A | 10/1989 | Conway et al. | |
| 4,892,519 A | 1/1990 | Songer et al. | |
| 4,898,591 A | 2/1990 | Jang et al. | |
| 4,921,483 A | 5/1990 | Wijay et al. | |
| 4,944,745 A | 7/1990 | Sogard et al. | |
| RE33,561 E | 3/1991 | Levy | |
| 5,037,404 A | 8/1991 | Gold et al. | |
| 5,047,045 A | 9/1991 | Arney et al. | |
| 5,078,702 A | 1/1992 | Pomeranz | |

(Continued)

FOREIGN PATENT DOCUMENTS

DE 94 20 821 4/1995

(Continued)

OTHER PUBLICATIONS

Restriction Requirement mailed on Mar. 17, 2008 for U.S. Appl. No. 11/136,251.

(Continued)

*Primary Examiner*—Nicholas D Lucchesi
*Assistant Examiner*—Aarti B Berdichevsky
(74) *Attorney, Agent, or Firm*—Baker Botts L.L.P

(57) ABSTRACT

The invention includes a catheter having an elongate main body having a proximal section and a distal section. The elongate main body further includes a plurality of stiffening members disposed along the length of the elongate main body. The plurality of stiffening members includes a first stiffening member and a second stiffening member. The first and second stiffening members can be disposed in an overlapping and spaced relationship. Alternatively, the second stiffening member can be disposed distal to the first stiffening member such that a gap is defined between the stiffening members.

25 Claims, 28 Drawing Sheets

U.S. PATENT DOCUMENTS

| | | |
|---|---|---|
| 5,102,403 A | 4/1992 | Alt |
| 5,135,535 A | 8/1992 | Kramer |
| 5,147,317 A | 9/1992 | Shank et al. |
| 5,154,725 A | 10/1992 | Leopold |
| 5,195,978 A | 3/1993 | Schiffer |
| 5,217,482 A | 6/1993 | Keith |
| 5,221,270 A | 6/1993 | Parker |
| 5,226,888 A | 7/1993 | Arney |
| 5,252,159 A | 10/1993 | Arney |
| 5,261,879 A | 11/1993 | Brill |
| 5,267,958 A | 12/1993 | Buchbinder et al. |
| 5,300,025 A * | 4/1994 | Wantink ............... 604/103.09 |
| 5,304,198 A | 4/1994 | Samson |
| 5,328,468 A | 7/1994 | Kaneko et al. |
| 5,334,147 A | 8/1994 | Johnson |
| 5,357,978 A | 10/1994 | Turk |
| 5,370,615 A | 12/1994 | Johnson |
| 5,395,334 A | 3/1995 | Keith et al. |
| 5,410,797 A | 5/1995 | Steinke et al. |
| 5,413,557 A | 5/1995 | Solar |
| 5,413,560 A | 5/1995 | Solar |
| 5,425,711 A | 6/1995 | Ressemann et al. |
| 5,443,457 A | 8/1995 | Ginn et al. |
| 5,460,185 A | 10/1995 | Johnson et al. |
| 5,470,315 A | 11/1995 | Adams |
| 5,480,383 A | 1/1996 | Bagaoisan et al. |
| 5,489,271 A | 2/1996 | Andersen |
| 5,490,837 A | 2/1996 | Blaeser et al. |
| 5,496,346 A | 3/1996 | Horzewski et al. |
| 5,500,180 A | 3/1996 | Anderson et al. |
| 5,538,510 A | 7/1996 | Fontirroche et al. |
| 5,545,138 A | 8/1996 | Fugoso et al. |
| 5,549,553 A | 8/1996 | Ressemann et al. |
| 5,549,563 A | 8/1996 | Kronner et al. |
| 5,588,964 A | 12/1996 | Imran et al. |
| 5,605,543 A | 2/1997 | Swanson |
| 5,634,902 A | 6/1997 | Johnson et al. |
| 5,649,909 A | 7/1997 | Cornelius |
| 5,656,029 A | 8/1997 | Imran et al. |
| 5,658,251 A | 8/1997 | Ressemann et al. |
| 5,662,622 A | 9/1997 | Gore et al. |
| 5,667,493 A | 9/1997 | Janacek |
| 5,669,932 A | 9/1997 | Fischell et al. |
| 5,695,483 A | 12/1997 | Samson |
| 5,702,439 A | 12/1997 | Keith et al. |
| 5,711,909 A | 1/1998 | Gore et al. |
| 5,728,067 A | 3/1998 | Enger |
| 5,733,400 A | 3/1998 | Gore et al. |
| 5,738,667 A | 4/1998 | Solar |
| 5,755,685 A | 5/1998 | Anderson |
| 5,755,687 A | 5/1998 | Donlon et al. |
| 5,775,685 A | 7/1998 | Yamaoka et al. |
| 5,807,355 A | 9/1998 | Ramzipoor et al. |
| 5,820,594 A | 10/1998 | Fontirroche et al. |
| 5,820,613 A | 10/1998 | Van Werven-Franssen et al. |
| 5,823,995 A | 10/1998 | Fitzmaurice et al. |
| 5,824,173 A | 10/1998 | Fontirroche et al. |
| 5,833,604 A | 11/1998 | Houser et al. |
| 5,836,965 A | 11/1998 | Jendersee et al. |
| 5,843,032 A | 12/1998 | Kastenhofer |
| 5,843,050 A | 12/1998 | Jones et al. |
| 5,851,464 A | 12/1998 | Davila et al. |
| 5,882,336 A | 3/1999 | Janacek et al. |
| 5,891,056 A | 4/1999 | Ramzipoor |
| 5,891,110 A | 4/1999 | Larson et al. |
| 5,902,290 A | 5/1999 | Peacock, III et al. |
| 5,951,539 A | 9/1999 | Nita et al. |
| 5,980,486 A | 11/1999 | Enger |
| 6,004,291 A | 12/1999 | Ressemann et al. |
| 6,010,521 A | 1/2000 | Lee et al. |
| 6,017,323 A | 1/2000 | Chee |
| 6,027,477 A | 2/2000 | Kastenhofer |
| 6,030,405 A | 2/2000 | Zarbatany et al. |
| 6,036,670 A | 3/2000 | Wijeratne et al. |
| 6,036,715 A | 3/2000 | Yock |
| 6,059,770 A | 5/2000 | Peacock, III et al. |
| 6,066,114 A | 5/2000 | Goodin et al. |
| 6,071,273 A | 6/2000 | Euteneuer et al. |
| 6,102,890 A | 8/2000 | Stivland et al. |
| 6,123,698 A | 9/2000 | Spears et al. |
| 6,129,708 A | 10/2000 | Enger |
| 6,159,229 A | 12/2000 | Jendersee et al. |
| 6,165,166 A | 12/2000 | Samuelson et al. |
| 6,187,130 B1 | 2/2001 | Berard et al. |
| 6,193,686 B1 | 2/2001 | Estrada et al. |
| 6,210,364 B1 | 4/2001 | Anderson et al. |
| 6,254,549 B1 | 7/2001 | Ramzipoor |
| 6,273,874 B1 | 8/2001 | Parris |
| 6,273,899 B1 | 8/2001 | Kramer |
| 6,283,939 B1 | 9/2001 | Anderson et al. |
| 6,306,105 B1 | 10/2001 | Rooney et al. |
| 6,306,124 B1 | 10/2001 | Jones et al. |
| 6,309,402 B1 | 10/2001 | Jendersee et al. |
| 6,319,244 B2 | 11/2001 | Suresh et al. |
| 6,344,029 B1 | 2/2002 | Estrada et al. |
| 6,361,529 B1 | 3/2002 | Goodin et al. |
| 6,368,302 B1 | 4/2002 | Fitzmaurice et al. |
| 6,402,720 B1 | 6/2002 | Miller et al. |
| 6,475,184 B1 | 11/2002 | Wang et al. |
| 6,475,209 B1 | 11/2002 | Larson et al. |
| 6,488,694 B1 | 12/2002 | Lau et al. |
| 6,527,789 B1 | 3/2003 | Lau et al. |
| 6,530,938 B1 | 3/2003 | Lee et al. |
| 6,565,588 B1 | 5/2003 | Clement et al. |
| 6,575,958 B1 | 6/2003 | Happ et al. |
| 6,575,993 B1 | 6/2003 | Yock |
| 6,579,278 B1 | 6/2003 | Bencini |
| 6,633,648 B1 | 10/2003 | Bauck |
| 6,648,854 B1 | 11/2003 | Patterson et al. |
| 6,652,507 B2 | 11/2003 | Pepin |
| 6,663,648 B1 | 12/2003 | Trotta |
| 6,685,720 B1 | 2/2004 | Wu et al. |
| 6,685,721 B1 | 2/2004 | Kramer |
| 6,692,460 B1 | 2/2004 | Jayaraman |
| 6,695,812 B2 | 2/2004 | Estrada et al. |
| 6,702,750 B2 | 3/2004 | Yock |
| 6,702,781 B1 | 3/2004 | Reifart et al. |
| 6,733,473 B1 | 5/2004 | Reifart et al. |
| 6,733,487 B2 | 5/2004 | Keith et al. |
| 6,770,038 B2 | 8/2004 | Balbierz et al. |
| 6,814,744 B2 | 11/2004 | Yang et al. |
| 6,818,001 B2 | 11/2004 | Wulfman et al. |
| 6,821,281 B2 | 11/2004 | Sherman et al. |
| 6,821,287 B1 | 11/2004 | Jang |
| 6,887,219 B2 | 5/2005 | Wantink |
| 6,893,417 B2 | 5/2005 | Gribbons et al. |
| 6,979,342 B2 | 12/2005 | Lee et al. |
| 7,001,358 B2 | 2/2006 | Fitzmaurice et al. |
| 7,025,258 B2 | 4/2006 | Chang |
| 7,037,291 B2 | 5/2006 | Lee et al. |
| 7,118,551 B1 | 10/2006 | Lee et al. |
| 7,309,334 B2 | 12/2007 | Von Hoffmann |
| 2001/0021840 A1 | 9/2001 | Suresh et al. |
| 2001/0034514 A1 | 10/2001 | Parker |
| 2002/0007146 A1 | 1/2002 | Omaleki et al. |
| 2003/0105427 A1 | 6/2003 | Lee et al. |
| 2003/0163082 A1 | 8/2003 | Mertens |
| 2004/0010243 A1 | 1/2004 | Klint |
| 2004/0019322 A1 | 1/2004 | Hoffmann |
| 2004/0193140 A1 | 9/2004 | Griffin et al. |
| 2004/0236367 A1 | 11/2004 | Brown et al. |
| 2005/0059292 A1 | 3/2005 | Hayashi et al. |
| 2005/0131387 A1 | 6/2005 | Pursley |
| 2005/0267408 A1* | 12/2005 | Grandt et al. ............ 604/103.04 |

| | | | |
|---|---|---|---|
| 2006/0270977 | A1 | 11/2006 | Fisher et al. |
| 2007/0016132 | A1* | 1/2007 | Oepen et al. ............. 604/96.01 |
| 2007/0016165 | A1* | 1/2007 | Von Oepen et al. ......... 604/525 |
| 2007/0021771 | A1* | 1/2007 | Oepen et al. ................ 606/194 |
| 2007/0083188 | A1* | 4/2007 | Grandt et al. ............... 604/524 |
| 2007/0167913 | A1 | 7/2007 | Elkins et al. |
| 2009/0018502 | A1* | 1/2009 | Reifart et al. .......... 604/103.04 |

FOREIGN PATENT DOCUMENTS

| | | |
|---|---|---|
| DE | 97 29 499 | 1/1999 |
| EP | 0 029 185 | 5/1981 |
| EP | 0 408 198 | 1/1991 |
| EP | 0 414 350 | 2/1991 |
| EP | 0 518 205 | 12/1992 |
| EP | 0 806 220 | 11/1997 |
| EP | 0 916 359 | 5/1999 |
| EP | 1 435 252 | 7/2004 |
| EP | 1 518 581 | 3/2005 |
| WO | WO 92/17236 | 10/1992 |
| WO | WO 98/56448 | 12/1998 |
| WO | WO 01/70321 | 9/2001 |
| WO | WO 2005/113047 | 12/2005 |
| WO | WO 2005/118044 | 12/2005 |
| WO | WO 2005/118045 | 12/2005 |
| WO | WO 2006/104591 | 10/2006 |

OTHER PUBLICATIONS

Response to the Restriction Requirement filed on Apr. 14, 2008 for U.S. Appl. No. 11/136,251.
Non-Final Rejection mailed on Jun. 2, 2008 for U.S. Appl. No. 11/136,251.
Response to the non-Final Rejection mailed on Jun. 2, 2008 filed on Sep. 2, 2008 for U.S. Appl. No. 11/136,251.
Examiner Interview Summary Record mailed on Dec. 17, 2008 for U.S. Appl. No. 11/136,251.
Interview Summary and Supplemental Amendment filed on Dec. 19, 2008 for U.S. Appl. No. 11/136,251.
Notice of Allowance mailed on Jan. 13, 2009 for U.S. Appl. No. 11/136,251.
Issue Fee Payment received on Mar. 20, 2009 for U.S. Appl. No. 11/136,251.
Restriction Requirement mailed on Mar. 13, 2008 for U.S. Appl. No. 11/136,640.
Response to the Restriction Requirement filed on Apr. 14, 2008 for U.S. Appl. No. 11/136,640.
Non-Final Rejection mailed on Jun. 2, 2008 for U.S. Appl. No. 11/136,640.
Response to the non-Final Rejection mailed on Jun. 2, 2008 filed on Sep. 2, 2008 for U.S. Appl. No. 11/136,640.
Examiner Interview Summary Record mailed on Dec. 16, 2008 for U.S. Appl. No. 11/136,640.
Interview Summary and Supplemental Amendment filed on Dec. 19, 2008 for U.S. Appl. No. 11/136,640.
Notice of Allowance mailed on Jan. 12, 2009 for U.S. Appl. No. 11/136,640.
Request for Continued Examination (RCE) filed on Mar. 20, 2009 for U.S. Appl. No. 11/136,640.
Notice of Allowance mailed on Jun. 8, 2009 for U.S. Appl. No. 11/136,640.
Non-Final Rejection mailed on Nov. 3, 2008 for U.S. Appl. No. 11/357,775.
Response to the non-Final Rejection mailed on Nov. 3, 2008 filed on Feb. 3, 2009 for U.S. Appl. No. 11/357,775.
Final Rejection mailed on May 18, 2009 for U.S. Appl. No. 11/357,775.
Request for Continued Examination (RCE) and Amendment after Final Rejection filed on Aug. 17, 2009 for U.S. Appl. No. 11/357,775.
Preliminary Amendment filed on Aug. 18, 2006 for U.S. Appl. No. 11/439,809.
Restriction Requirement mailed on Jul. 29, 2008 for U.S. Appl. No. 11/439,809.
Response to the Restriction Requirement filed on Aug. 25, 2008 for U.S. Appl. No. 11/439,809.
Non-Final Rejection mailed on Sep. 3, 2008 for U.S. Appl. No. 11/439,809.
Notice of Abandonment mailed on May 1, 2009 for U.S. Appl. No. 11/439,809.
Non-Final Rejection mailed on Nov. 14, 2008 for U.S. Appl. No. 11/439,591.
Response to the non-Final Rejection mailed on Nov. 14, 2008 filed on Feb. 17, 2009 for U.S. Appl. No. 11/439,591.
Notice of Non-Compliant Amendment mailed on Mar. 25, 2009 for U.S. Appl. No. 11/439,591.
Response to the non-Final Rejection mailed on Nov. 14, 2008 filed on Apr. 16, 2009 for U.S. Appl. No. 11/439,591.
Final Rejection mailed on Jul. 24, 2009 for U.S. Appl. No. 11/439,591.
Non-Final Rejection mailed on Nov. 4, 2008 for U.S. Appl. No. 11/439,592.
Response to the non-Final Rejection mailed on Nov. 4, 2008 filed on Feb. 4, 2009 for U.S. Appl. No. 11/439,592.
Final Rejection mailed on May 19, 2009 for U.S. Appl. No. 11/439,592.
Request for Continued Examination (RCE) and Amendment after Final Rejection filed on Aug. 17, 2009 for U.S. Appl. No. 11/439,592.
Preliminary Amendment filed on Aug. 18, 2006 for U.S. Appl. No. 11/439,596.

* cited by examiner

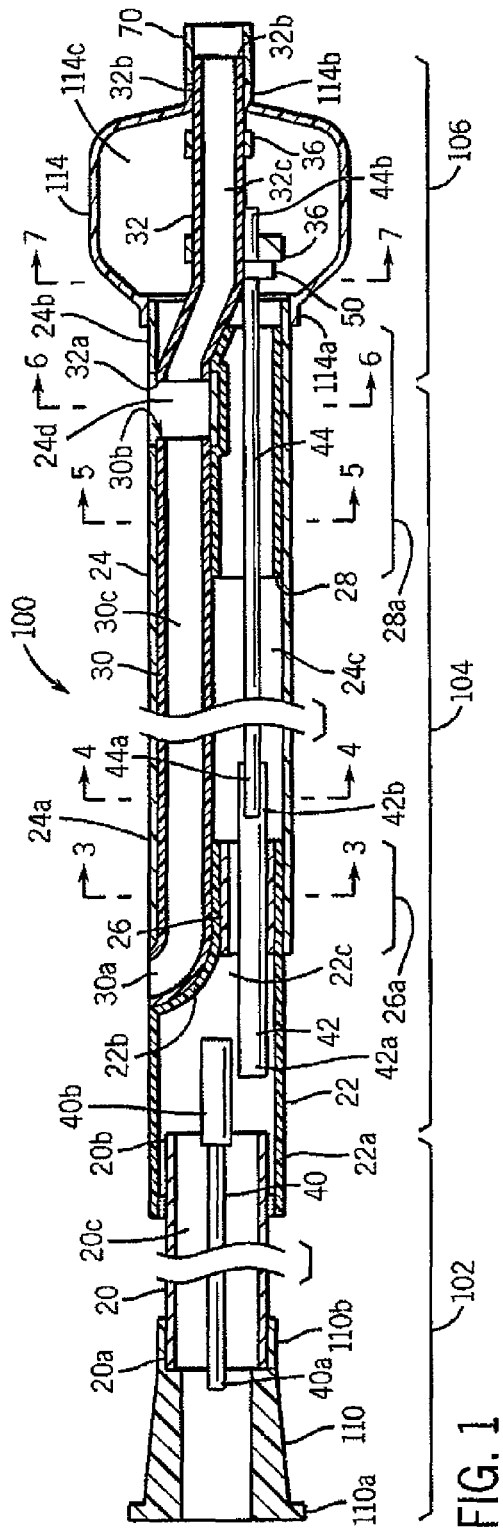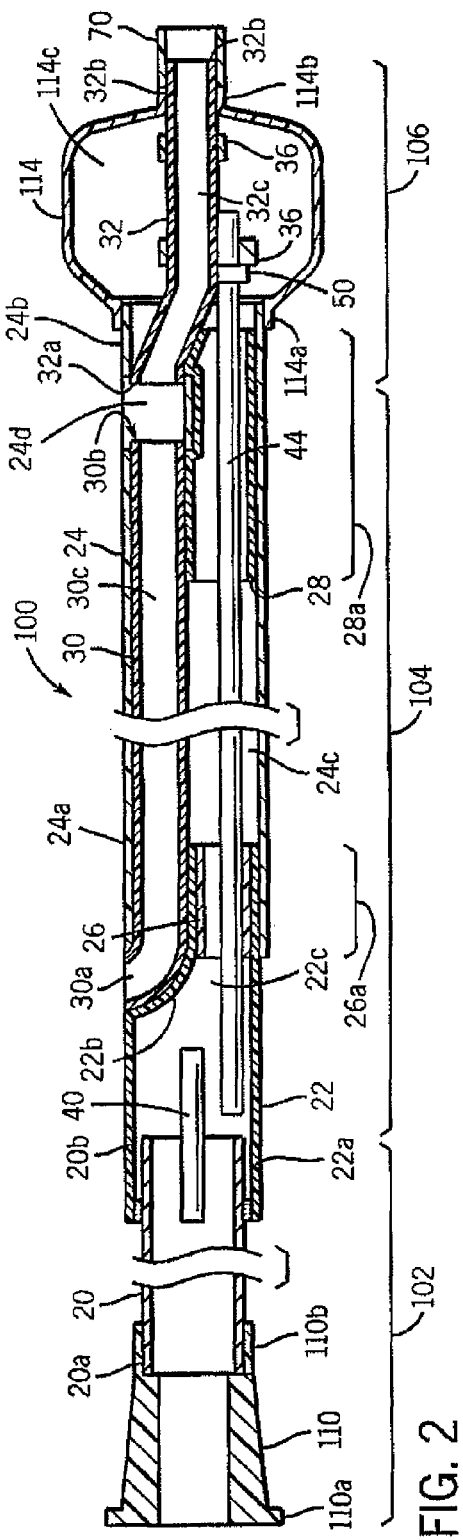

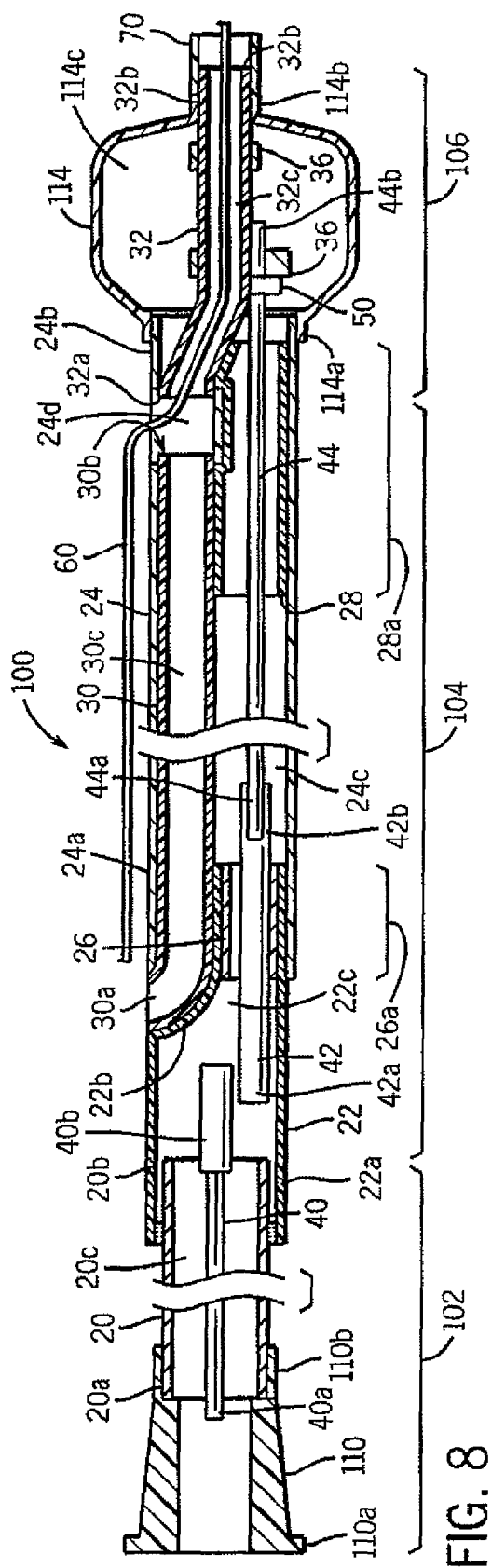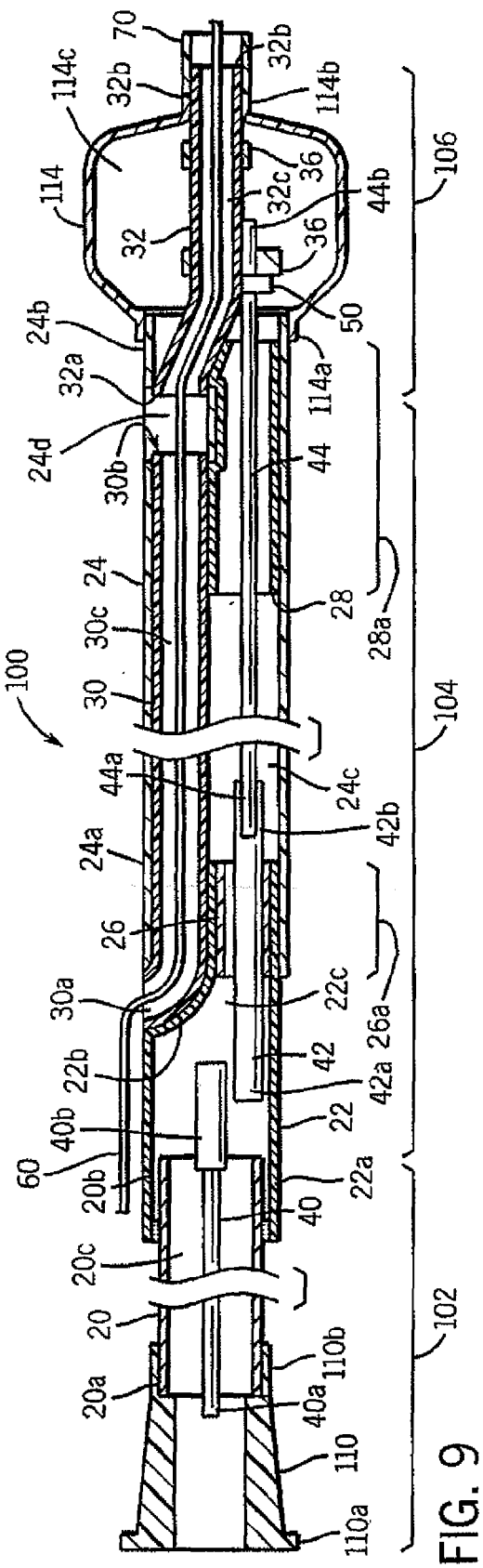
FIG. 8
FIG. 9

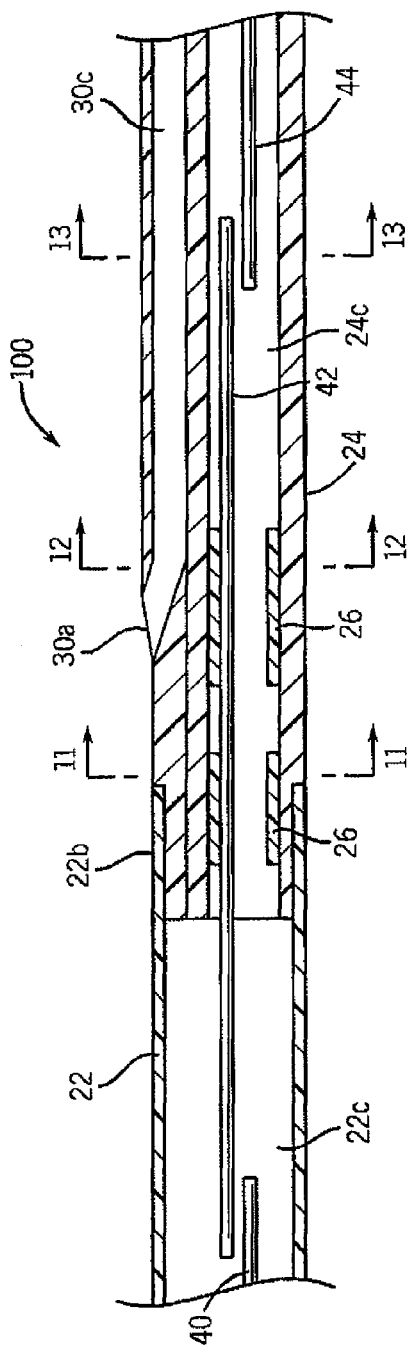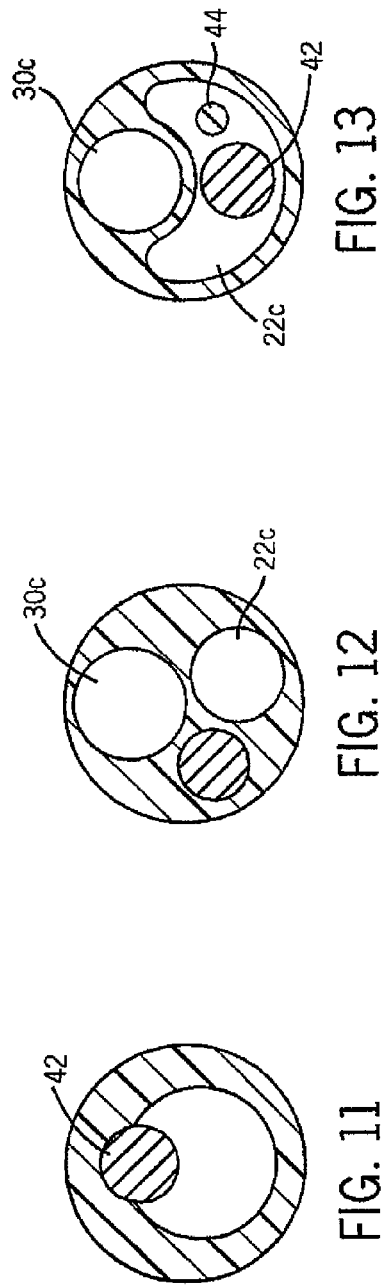
FIG. 10
FIG. 11
FIG. 12
FIG. 13

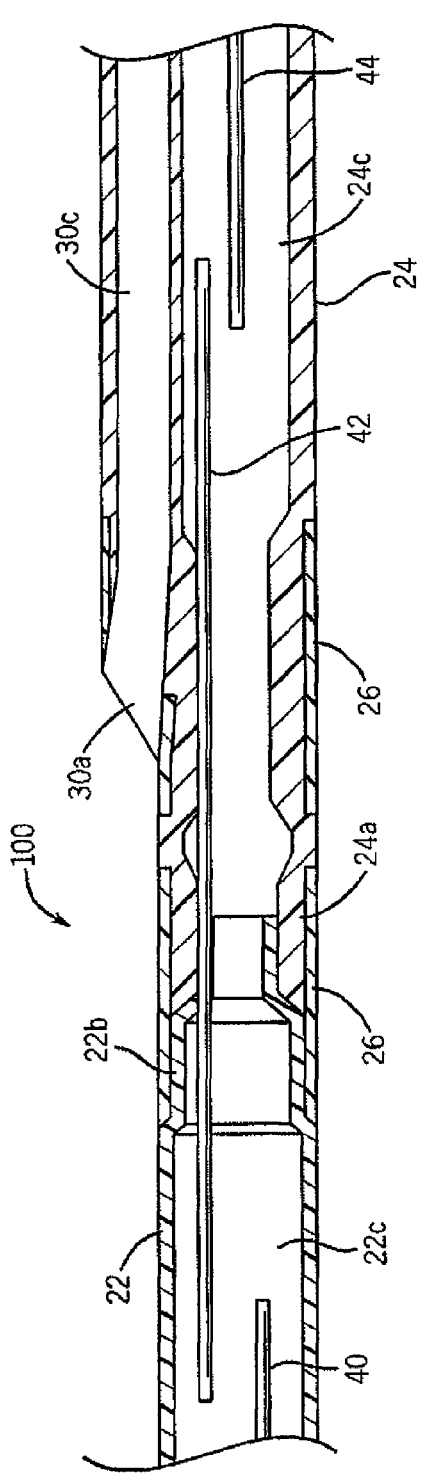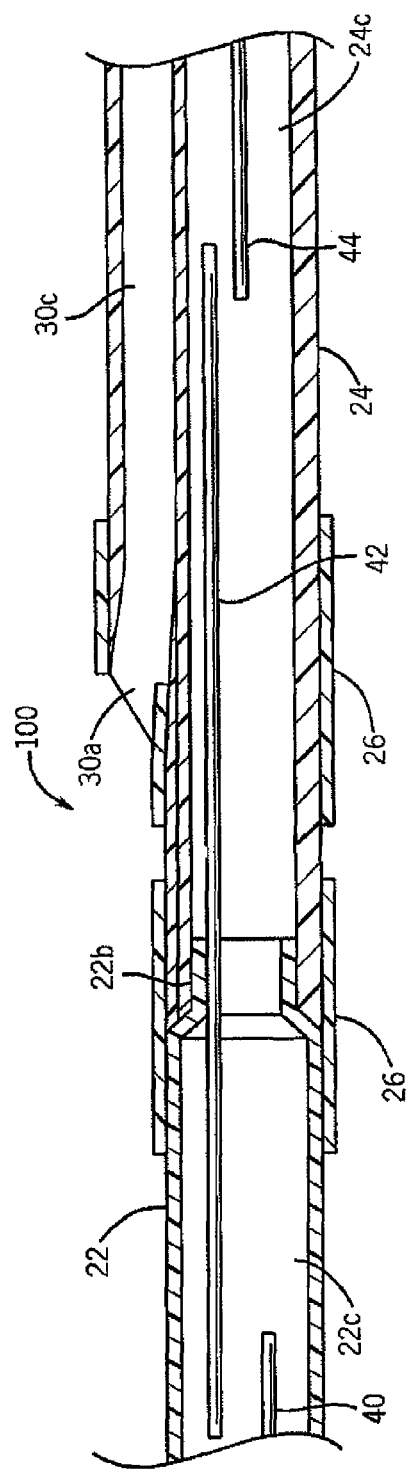

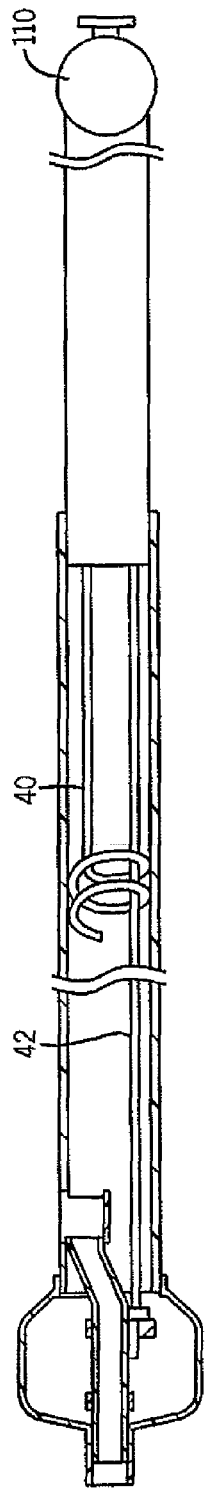
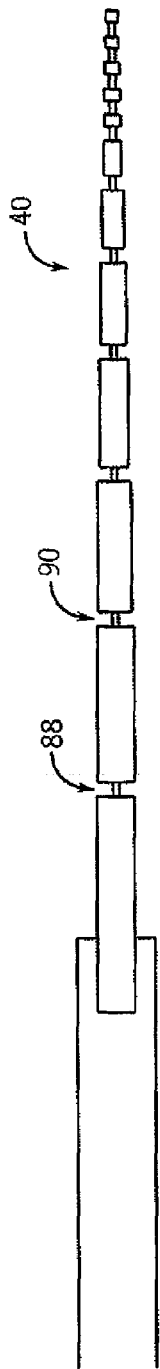
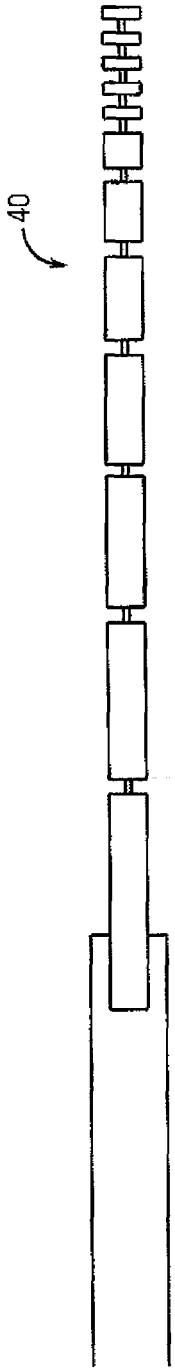
FIG. 18I
FIG. 19A
FIG. 19B

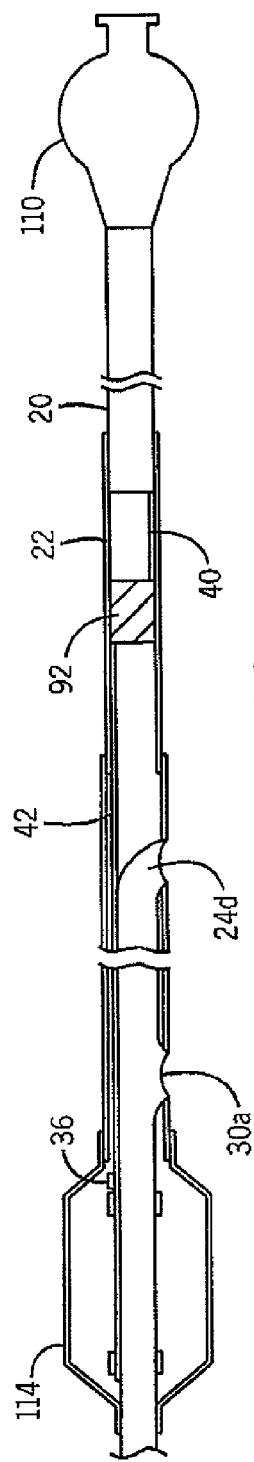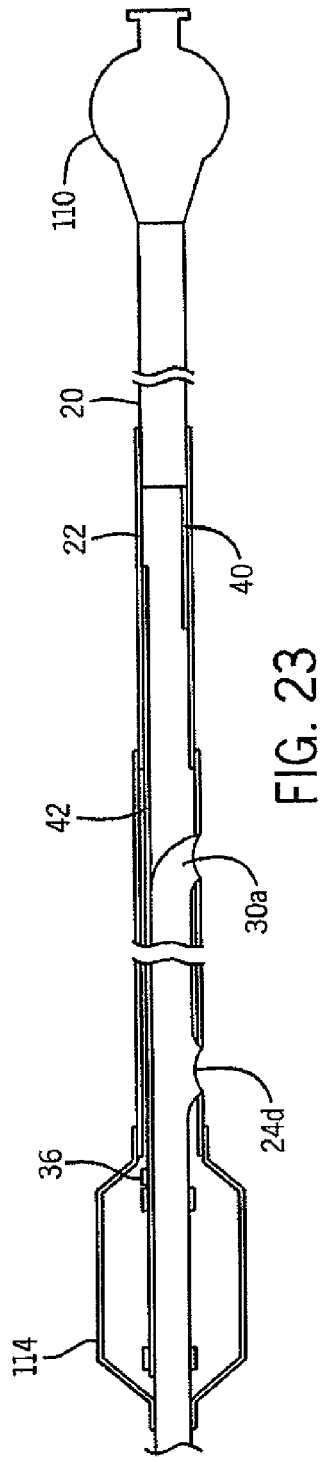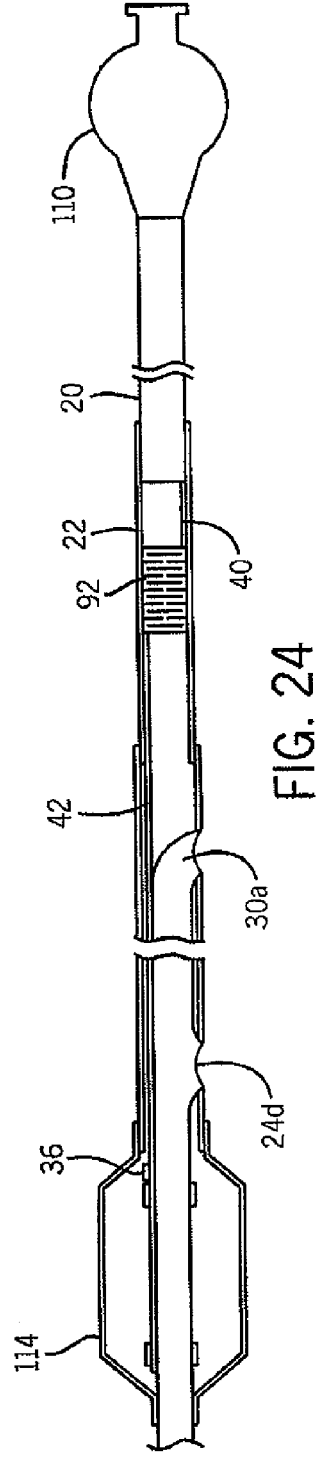

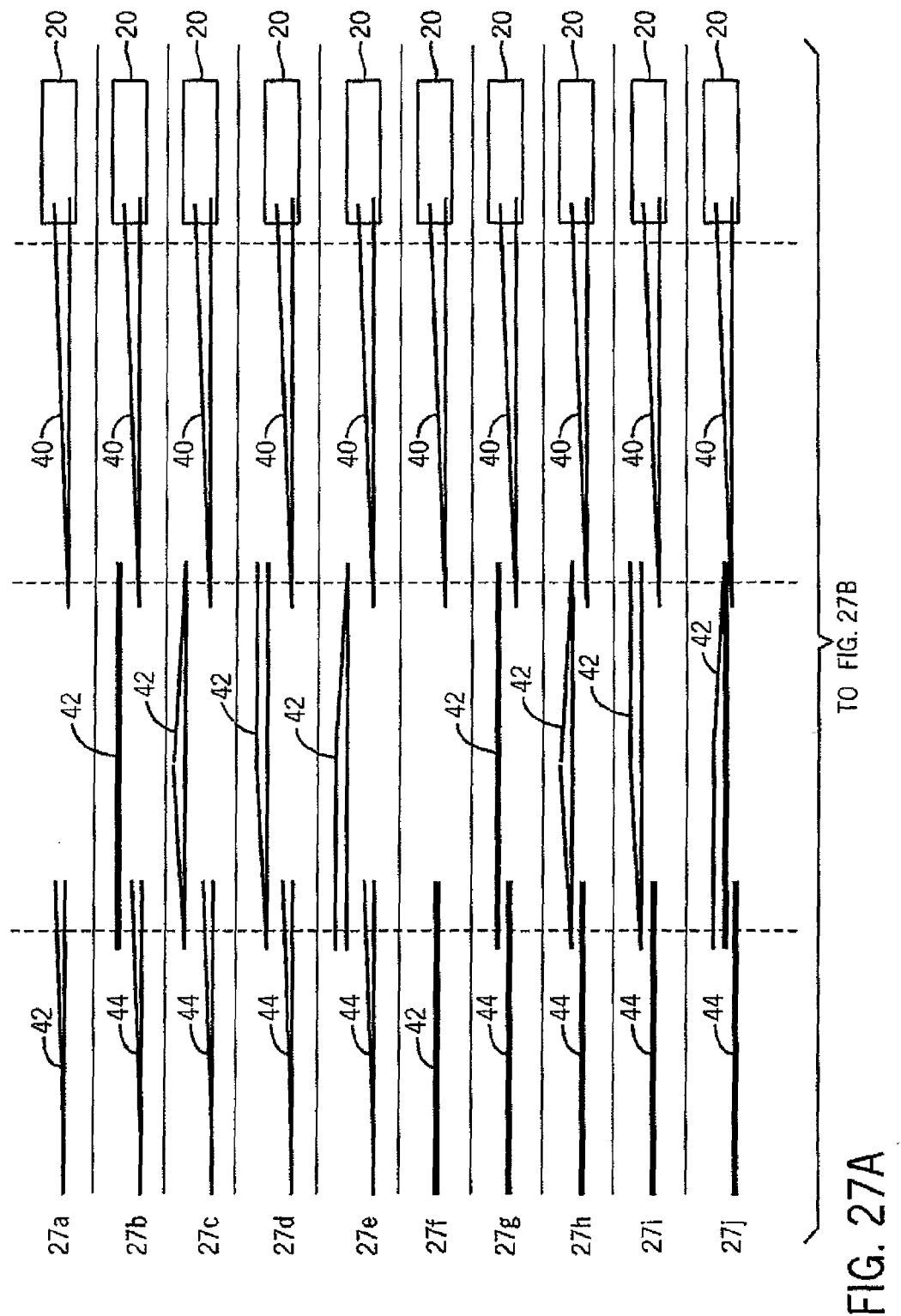

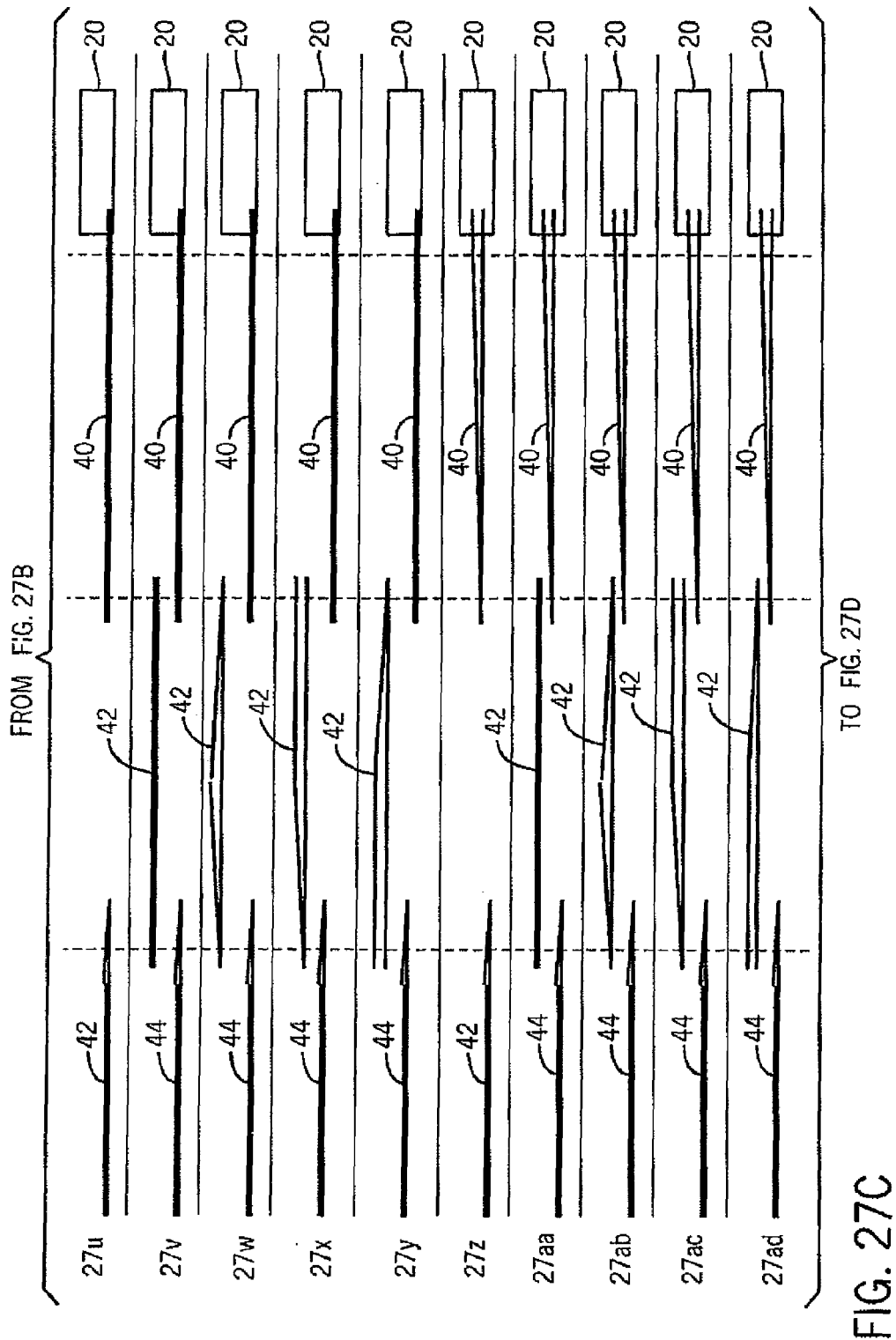

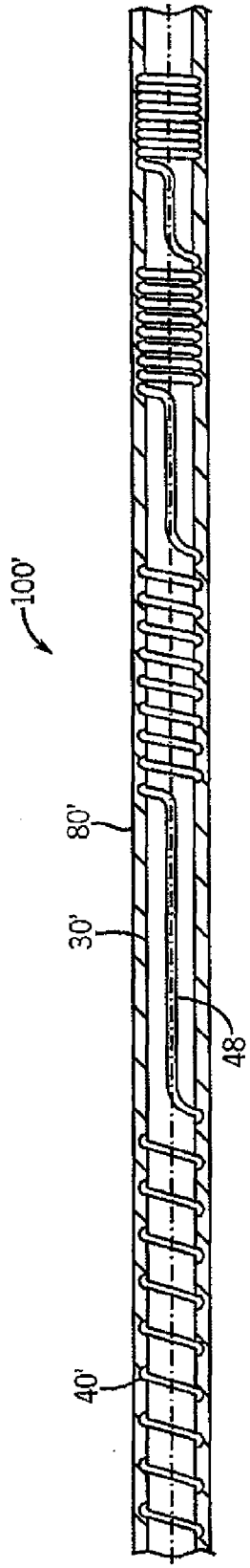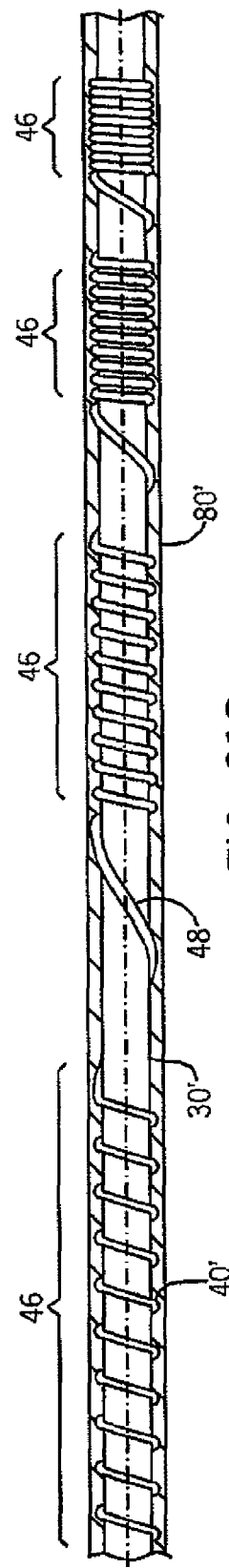
FIG. 31A
FIG. 31B

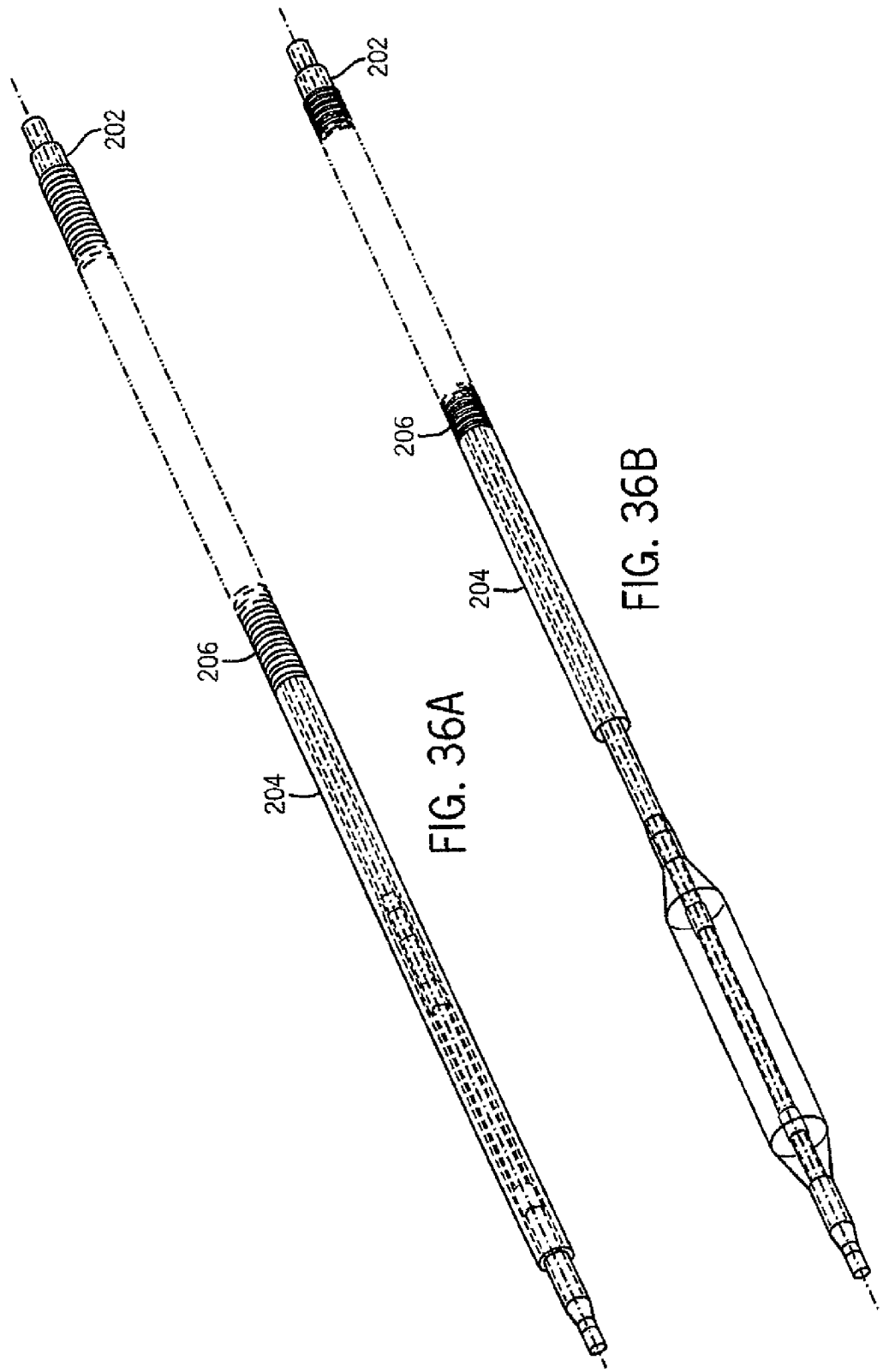

CATHETER HAVING PLURALITY OF STIFFENING MEMBERS

CROSS REFERENCE TO RELATED APPLICATIONS

This application claims the benefit of U.S. Provisional Patent Application Ser. No. 60/684,135, filed May 23, 2005 and is a continuation-in-part of U.S. patent application Ser. No. 11/136,640, filed May 23, 2005 now U.S. Pat. No. 7,625, 353, and which claims the benefit of U.S. Provisional Patent Application Ser. Nos. 60/575,643 filed on May 27, 2004, and 60/654,022 filed on Feb. 17, 2005, the entire contents of each are incorporated herein by reference.

BACKGROUND OF INVENTION

1. Field of Invention

The present invention relates to a catheter for treating a luminal system of a patient. Particularly, the present invention is directed to a catheter having a plurality of stiffening members to vary the stiffness along the length of the catheter body.

2. Description of Related Art

A variety of catheter devices are known in the art for treating the luminal system of a patient. Of such devices, many are directed to treating the cardiovascular system of a patient. One such cardiovascular system treatment includes percutaneous transluminal coronary angioplasty (PTCA); a procedure for treating heart disease. This procedure generally entails introducing a catheter assembly into the cardiovascular system of a patient via the brachial or femoral artery, and advancing the catheter assembly through the coronary vasculature until a balloon portion thereon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the catheter assembly to be withdrawn from the vasculature.

Often the site of the occlusive lesion is only reached by a tortuous pathway through the vasculature of the patient. The difficulty in accessing such regions requires that a successful catheter must be quite flexible to follow the tortuous path into the tissue, and at the same time, stiff enough to allow the distal end of the catheter to be manipulated from an external access site.

To address this problem, catheters having varied flexibility along their length have been developed. For example, each of U.S. Pat. No. 4,782,834 to Maguire and U.S. Pat. No. 5,370,655 to Burns discloses a catheter having sections along its length which are formed from materials having a different stiffness; U.S. Pat. No. 4,976,690 to Solar discloses a catheter having an intermediate waist portion which provides increased flexibility along the catheter shaft; U.S. Pat. No. 5,423,754 to Cornelius discloses a catheter having a greater flexibility at its distal portion due to both a material and dimensional transition in the shaft; and U.S. Pat. No. 5,649,909 to Cornelius discloses a catheter having a proximal portion with greater stiffness due to the application of a polymeric coating thereto.

Such conventional methods and systems generally have been considered satisfactory for their intended purpose. However, catheters still suffer from certain performance issues, such as by lack of pushability and kink resistance. Although solutions to this problem have been developed as discussed supra, there still remains a continued need in the art for a catheter having varied flexibility to enhance pushability, kink resistance and versatility. The present invention provides a solution for these problems.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied herein and broadly described, the invention includes a catheter having an elongate main body having a proximal end and a distal end. The elongate main body has at least a proximal section and a distal section. The elongate main body further includes a plurality of stiffening members disposed along a length of the elongate main body. The plurality of stiffening members includes a first stiffening member and a second stiffening member, each stiffening member having a proximal end and a distal end. The first stiffening member is disposed in an overlapping spaced relationship relative to the second stiffening member. Optionally, the elongate main body can further include additional stiffening members disposed along a length of the elongate main body with each additional stiffening member being disposed in an overlapping spaced relationship relative to another stiffening member.

In further accordance with the invention, at least one stiffening member can be secured to the catheter in a variety of ways. For example and not limitation, the at least one stiffening member can be secured to an adapter, e.g., luer, hub, manifold, or a reinforcement or filler material, or support member. Alternatively, the at least one stiffening member can be secured to the elongate main body by way of an engagement member. In this manner, an engagement member can be secured to the surface of the elongate main body such that a space or cavity is defined for engaging the at least one stiffening member.

In accordance with a further aspect of the invention, the catheter includes a plurality of stiffening members configured to control or vary axial flexibility along a length of the elongate main body. The plurality of stiffening members can include a first stiffening member and a second stiffening member, each stiffening member having a different flexibility. For example and not limitation, the second stiffening member can be configured to have a greater flexibility than the first stiffening member to define a catheter having greater flexibility distally along its length. Alternatively, the first stiffening member can be configured to have a greater flexibility than the second stiffening member to define a catheter having a greater stiffness distally along its length, if desired. Further, the plurality of stiffening members can include a third stiffening member having a flexibility different than at least one of the first and second stiffening members.

The plurality of stiffening members can be configured to control or vary the flexibility along the elongate main body in a variety of ways. For example, a first stiffening member and a second stiffening member can each be formed from a material having a different flexibility. In this regard, each of the plurality of stiffening members can be formed from a variety of materials including but not limited to metal, metal alloy, polymer, composite, carbon, and reinforced materials. Notably, the stiffening member can be in the form of a wire, strand, rod, tubular member, filament and the like.

As yet another alternative, the flexibility or bending stiffness of the catheter or a portion of the catheter can be varied depending on the orientation of the stiffening member and the catheter portion. For example, if the stiffening member is oriented such that it is centrally located within a lumen of a tubular member, the stiffness of the tubular member would be relatively uniform across the length of the tubular member when the tubular member is in a bending orientation. However, if the stiffening member is attached or secured to the inner wall of the tubular member, the tubular member would have a variation in stiffness along its length depending on the direction the catheter is bent.

At least one of the plurality of stiffening members can include a reduced cross-sectional area or an increased cross sectional area along its length, if desired. In this manner, any of the stiffening members can be configured to include a distal taper, a proximal taper, or include a taper at its distal and proximal ends.

Alternatively, at least one of the plurality of stiffening members can include at least one cut or a plurality of cuts defined along its length. The at least one cut or plurality of cuts can be, for example, a circumferential cut or a longitudinal cut along the length of the stiffening member. Each of the plurality of circumferential cuts along the length of the stiffening member define at least one circumferential groove which are spaced along the length of the stiffening member. The spacing between adjacent grooves can be varied along the length of the stiffening member to define a stiffening member having a varied flexibility along its length, if desired. Alternatively, the spacing between adjacent grooves can be substantially similar along the length of the stiffening member.

The plurality of longitudinal cuts along a length of the stiffening member can include at least a first longitudinal cut and a second longitudinal cut having a different length.

Moreover, the plurality of stiffening members can have a variety of configurations, such as linear configurations and non-linear configurations. In this regard, the non-linear configuration can include a wavy configuration and a helical configuration. Moreover, at least one stiffening member can include a linear configured portion and a non-linear configured portion along its length.

At least one stiffening member can be disposed circumferentially about the outer surface of the tubular member to define at least one cluster, which includes a plurality of helical turns or rotations having a pitch and circumferentially disposed about a section of the tubular member along a length of the cluster. The helical turns associated with an individual cluster are configured to have a predetermined pitch. The pitch can be varied or constant along the length of the cluster. For example, the varied pitch can include helical turns having an increasing pitch along the length of the cluster or a decreasing pitch along the length of the cluster. Further, the helical turns can include a constant pitch along the length of the catheter.

The at least one cluster may include a plurality of clusters along the length of the tubular member configured to control or vary axial flexibility along a length of the tubular member. The plurality of clusters can include a first cluster including a first plurality of helical turns and a second cluster including a second plurality of helical turns, each cluster having a different flexibility. For example and not limitation, the second cluster can be configured to have a greater flexibility than the first cluster to define a tubular member having greater flexibility along its length. Alternatively, the first cluster can be configured to have a greater flexibility than the second cluster to define a catheter having greater stiffness along its length, if desired.

The plurality of clusters can be configured to control or vary the flexibility along the tubular member in a variety of ways. For example, a first cluster including a first plurality of helical turns can be configured to have a first pitch and a second cluster including a second plurality of helical turns can be configured to have a second pitch. The first cluster can be associated with a first section of the tubular member and the second cluster can be associated with a second section of the tubular member. In this regard, the first and second plurality of helical turns can each be configured to include a pitch that is constant along the length of the first cluster and second cluster, respectively. The first plurality of helical turns can be configured to have a longer pitch than the pitch of the second plurality of helical turns. In this manner, the first section of the tubular member is configured to have a greater flexibility than the second section of the tubular member due to the orientation of the first and second clusters relative to the tubular member, and the configuration of the first and second plurality of helical turns and their respective first and second pitches along the length of the corresponding cluster. The first cluster can be disposed at the distal section of the tubular member and the second cluster can be disposed at a proximal section of the tubular member to define a tubular member having an increased flexibility along its distal length. Alternatively, the first cluster can be disposed at a proximal section of the tubular member and the second cluster can be disposed at a distal section of the tubular member to define a tubular member having an increasing stiffness along its distal length.

Alternatively, the plurality of clusters can each be formed from a material having a different flexibility to control and vary the flexibility along the tubular member. For example, a first cluster including a first plurality of helical turns and a second cluster having a second plurality of helical turns can each be formed from a material having a different flexibility.

In accordance with the invention, the plurality of clusters can comprise multiple elements joined by interconnectors. The interconnectors can be linear or non-linear members. Alternatively, the at least one stiffening member can be a single element helically disposed along the length of the tubular member configured to include at least one cluster.

Further, the cluster including helical turns can be formed from a variety of materials including but not limited to metal, metal alloy, polymeric material, composite material, carbon, fiber reinforced materials. The cluster including helical turns can be in the form of a wire, strand, rod, filament, tubular member and the like.

In accordance with a further aspect of the invention, the tubular member can include a coating applied to the outer surface of the tubular member. In this regard, the coating can be a topcoat to overlie the at least one stiffening member so as to provide a tubular member having a smooth outer surface, a base layer directly contacting the outer surface of the tubular member or the coating can include multiple coatings to provide a topcoat and a base layer.

In accordance with a further aspect of the invention, a catheter is provided which comprises an elongate main body including at least a proximal section and a distal section, each of the proximal section and the distal section of the elongate main body having a lumen defined therethrough. The catheter further includes a guidewire tube defining a guidewire lumen extending through at least a portion of the distal section of the elongate main body. The proximal section includes a hypotube and the distal section includes an inflatable member. A plurality of stiffening members is disposed along a length of the elongate main body.

In accordance with a further aspect of the invention, the catheter can further include at least one reinforcement member to reinforce a section of the elongate main body. The at least one reinforcement member can be disposed adjacent to or near at least one guidewire port disposed across the elongate main body. In one embodiment, the reinforcement member can be added to the elongate main body to reinforce the elongated main body at a welding area. Alternatively, the at least one reinforcement member can be disposed between two components along the elongate main body at a welding region to secure the components of the elongated main body and tightly seal the welding region. The reinforcement member can provide added material to the wall of the elongate main body and help to avoid thinning of the wall of the elongate main body during welding or other processes. Avoidance of wall thinning of the elongate main body therefore provides a tight seal, even when high pressure is applied in the lumen of the elongate main body. Accordingly, in one embodiment, the reinforcement member is a sealing member to seal a section of the elongate main body. The reinforcing member can be, for example, a tubular member or filler material.

The plurality of stiffening members includes a first stiffening member and a second stiffening member. The first stiffening member can be disposed in an overlapping and spaced relationship with the second stiffening member. Alternatively, the second stiffening member can be disposed distal of the first stiffening member such that a gap is defined between the stiffening members. If desired, a support member can be disposed between the first and second stiffening members.

In accordance with one aspect of the invention, the distal end of at least one of the plurality of stiffening members has a length extending within the inflatable member. The guidewire tube can extend within the inflatable member and the catheter can further include at least one marker band disposed circumferentially around an outer surface of the guidewire tube. At least a portion of at least one of the plurality of stiffening members can be disposed between the outer surface of the guidewire tube and an inner surface of the at least one marker band. The at least one of the plurality of stiffening members an be slidingly received between the outer surface of the guidewire tube and the inner surface of the marker band.

The at least one of the plurality of stiffening members can further include a protrusion disposed along its length. The protrusion can be disposed proximate the distal end of the stiffening member and provide a butting engagement with the marker band.

In yet another aspect of the invention, a process is provided in which a balloon having a tapered profile is achieved. The process includes providing a tubular member formed of a material having an outer surface, a proximal region, a distal region, and an intermediate region therebetween. A recess is defined at a predetermined targeted site on the outer surface of the tubular member. The recess is formed by removing a predetermined amount of material from the target site. The target site is predetermined to correspond to a portion of a balloon, formed from the tubular member, at which a tapered profile is desired. For example, the predetermined target site can correspond to the conical, waist, or working portions of the balloon. Accordingly, a balloon having a cone portion, waist portion, and/or working portion having a tapered profile can be configured from the tubular member. In one preferred embodiment, the material is removed by laser ablation.

In a further aspect of the invention, a sheath is provided for a balloon catheter. In one embodiment, the sheath is configured to be utilized with a rapid exchange type balloon catheter. The sheath includes a proximal sheath section and a distal sheath section. The proximal sheath section is stationary and is configured to overlie a proximal portion of the rapid exchange catheter. In this regard, the stationary sheath section covers at least the proximal port disposed in the sidewall of the catheter body. Preferably, the proximal sheath section includes an opening along its length that corresponds in location with the proximal port disposed in the sidewall of the catheter body so as to provide accessibility to the proximal port. The distal sheath section is retractable and overlies at least the balloon portion of the catheter. In operation, the distal sheath section is retracted by actuation of an actuator such as a pull-wire or other mechanism. During retraction, the distal sheath section slides proximally toward the stationary sheath section to expose the balloon. For example, the distal sheath section can be configured to telescopically slide over a surface of the proximal sheath section. Alternatively, the distal sheath section can be a compressible bellow member. In operation, the distal sheath has a length that compresses proximally to expose the balloon portion of catheter.

The sheath can further include an intermediate sheath section disposed between proximal and distal sheath sections. In this manner, the intermediate sheath section is a bellowed sheath section operatively connected to the proximal and distal sheath sections. In operation, the bellowed sheath is proximally compressed and proximally displaces the distal sheath section to expose the balloon section of the catheter.

In further accordance with the invention, an actuator can be a pull wire that is operatively attached to the distal sheath section or the intermediate sheath section. The pull wire can be disposed in at least a portion of the catheter shaft. For example and not limitation, the pull wire can be disposed in the proximal portion of the inflation lumen of the catheter. In this manner, a distal section of the pull wire exits the catheter body at an intermediate section of the catheter body and extends distally exteriorly along the outer surface of the catheter body. In this regard, the proximal sheath section covers the portion of the pull wire that is disposed exterior to the catheter body. The portion of the pull wire that is disposed in the lumen of the catheter shaft can be disposed in a dedicated lumen or can be secured to the inner surface of the lumen of the catheter.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

FIG. 1 is a schematic view of a first representative embodiment of a catheter having an elongate main body including a proximal section, a distal section, and a plurality of stiffening members in accordance with the present invention;

FIG. 2 is a schematic view of another representative embodiment of a catheter having an elongate main body including a proximal section, a distal section and a plurality of stiffening members in accordance with the present invention;

FIG. 8 is a side view of the catheter of FIG. 1 including a guidewire disposed in a first guidewire tube;

FIG. 9 is a side view of the catheter of FIG. 9 including the guidewire disposed in each of first and second guidewire tubes in accordance with the invention;

FIG. 10 is a schematic side view of another representative embodiment of a catheter in accordance with the present invention;

FIG. 11 is a cross sectional view at line 11-11 of the catheter of FIG. 10 in accordance with the present invention;

FIG. 12 is a cross sectional view at line 12-12 of the catheter of FIG. 10 in accordance with the present invention;

FIG. 13 is a cross sectional view at line 13-13 of the catheter of FIG. 10 in accordance with the present invention;

FIG. 15 is a schematic side view of another embodiment of a catheter in accordance with the present invention;

FIG. 16 is a schematic representation of the embodiment of FIG. 15 in accordance with the present invention;

FIG. 18I is a schematic side view of an alternative embodiment of a catheter having a plurality of stiffening members in accordance with the present invention.

FIG. 19A is a schematic side view of a stiffening member having a plurality of cuts and a reduced cross sectional area along the length thereof in accordance with the present invention;

FIG. 19B is a schematic side view of a stiffening member having a plurality of cuts along a length thereof in accordance with the present invention;

FIG. 22 is a schematic side view of a catheter having a plurality of stiffening members in accordance with the invention;

FIG. 23 is a schematic side view of a catheter having first and second stiffening members disposed in an overlapping and spaced relation in accordance with the invention;

FIG. 24 is a schematic side view of a catheter having a tubular member disposed between a plurality of stiffening members in accordance with the invention;

FIGS. 27A to 27D show schematic views of alternative embodiments 27a-27aj, each with a plurality of stiffening members in accordance with the present invention;

FIGS. 31A and 31B each schematically depict a tubular member having at least one stiffening member circumferentially disposed about the tubular member and a coating thereon in accordance with the invention;

FIGS. 36A and 36B schematically depict another embodiment of a sheath in accordance with the invention.

DETAILED DESCRIPTION OF THE PREFERRED EMBODIMENT

Figure 3:
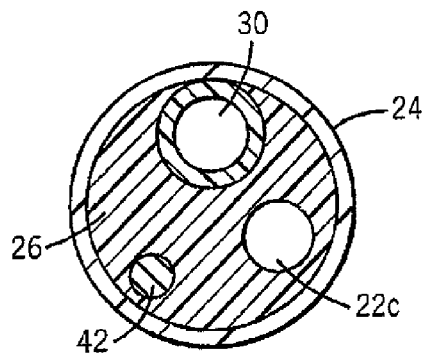
FIG. 3 is a cross sectional view at line 3-3 of the catheter of FIG. 1 in accordance with an embodiment of the present invention.

Reference will now be made in detail to the present preferred embodiments of the invention, an example of which is illustrated in the accompanying drawings. The method and corresponding steps of the invention will be described in conjunction with the detailed description of the system.

The devices and methods presented herein may be used for treating the luminal systems of a patient. The present invention is particularly suited for treatment of the cardiovascular system and the peripheral system of a patient. The treatment of the cardiovascular system includes the performance of angioplasty or delivery of balloon-expandable or self-expanding interventional devices (e.g., stents, filters, coils). The treatment of the peripheral system includes treatment of the carotid, popliteal and renal vessels. Accordingly, the present invention is also suitable for special endovascular vessels.

In accordance with the invention, a catheter is provided having an elongate main body. Generally, the elongate main body has at least a proximal section and a distal section. The catheter further includes a plurality of stiffening members including a first stiffening member and a second stiffening member. The first stiffening member is disposed in an overlapping and spaced relationship relative to the second stiffening member.

For purpose of explanation and illustration, and not limitation, an exemplary embodiment of the catheter in accordance with the invention is shown in FIG. 1 and is designated generally by reference character 100. Additional features, aspects and embodiments of a catheter in accordance with the invention are provided in FIGS. 2 to 36 as will be described.

For purposes of illustration and not limitation, as embodied herein and as depicted in FIG. 1, catheter 100 has a main body portion including a proximal section 102, a distal section 106, and an intermediate section 104 disposed between the proximal and distal sections. Each section having a proximal end and a distal end.

Generally, the proximal section of the catheter 100 includes adapter 110 secured to proximal tubular member 20. Proximal tubular member 20 has a body including an outer surface, proximal end region 20a, distal end region 20b and inflation lumen 20c therebetween. Proximal end region 20a of proximal tubular member 20 is secured to adapter 110 by suitable structure or method. For example and not limitation, proximal tubular member can be affixed to adapter 110 by fusion, welding, overmolding, e.g., injection molding, or adhesive. Additionally, and as schematically depicted in FIG. 1, adapter 110 can have a distal end 110b in overlapping relation with a portion of proximal tubular member 20. Adapter 110 can be a hub or a handle, a manifold, or can be a luer fitting for connection with an inflation/deflation device, such as a syringe (not shown).

Proximal tubular member 20 can be made of any suitable material, such as metal, metal alloy, carbon, carbon reinforced materials, metal reinforced polymers, boron fiber reinforced materials, glass reinforced materials, aramid fiber reinforced materials, ceramic, composite, Kevlar, or polymer as described further below. The method of joining the adapter 110 and proximal tubular member 20 will depend on the materials used. Preferably, proximal tubular member 20 further includes lumen 20c extending therethrough in fluid communication with adapter 110.

If desired, catheter 100 can include a strain relief (not shown), which extends from adapter 110 and is disposed along at least a portion of proximal tubular member 20 to provide increased resistance to kinking between the adapter and the proximal tubular member. The strain relief is preferably formed of a polymeric material and extends distally along at least a length of proximal tubular member 20. The strain relief can be formed as a separate sleeve, or overmolded onto the proximal tubular member 20. A variety of materials can be used for the strain relief including polymers such as but not limited to FEP, PTFE, polyamide, and PEEK, and metals such as but not limited to stainless steel, and nitinol, e.g., spring.

The method or structure for joining proximal tubular member 20 to intermediate tubular member 22 will depend upon the materials used. For example, adhesive, welding, fusion, RF bonding, or other bonding techniques can be employed. Particularly, if the proximal tubular member is formed from metal and the adjacent tubular member is formed from a polymeric material, the polymeric tubular member can be joined to the metallic tubular member by utilization of a compression tool such as but not limited to a jaw press.

In one preferred embodiment, proximal tubular member 20 is a hypotube made of metal, such as stainless steel, and intermediate tubular member is a polymer, such as nylon. In this embodiment, distal region 20b includes an outer surface having a bonding region defined by a roughened outer surface across a length of the proximal tubular member (not shown). The roughened outer surface can be prepared by for example grit blasting or knurling a portion of the outer surface known techniques. Preferably the bonding region has a length of at least approximately 10 to 20 mm to facilitate securing an adjacent tubular member to proximal tubular member 20. The bonding region can be provided at the distal end of the proximal tubular member 20 or, if desired, can be spaced proximal from the distal end. In further accordance with this embodiment, proximal region 22a of intermediate tubular member 22 can be configured to overlap at least a portion of the bonding region disposed on the outer surface of proximal tubular member 20. For example, and not limitation, intermediate member can overlap the entire length of the bonding region defined by the roughened surface or a portion thereof.

Distal region 20b is secured to an adjacent tubular member, such as intermediate tubular member 22, as depicted in FIGS. 1 and 2, by suitable structure or method. As shown schematically in FIG. 1, proximal end region 22a of intermediate tubular member 22 can be configured to form a lap joint such that proximal end region 22a includes a proximal end that overlaps at least a portion of the distal end region 20b of proximal tubular member 20.

Similarly, it is not required that the bond securing proximal tubular member to intermediate tubular member have a length equivalent to the length of the roughened surface. For the purpose of illustration and not limitation, the proximal region of intermediate member can be configured to overlap an entire length of the roughened surface, for example 10 cm, but have a bonding length of only about 1 cm in the proximal portion of the bonding region length. Accordingly, the intermediate tubular member 22 can be configured to bond to only a portion of the bonding region that is proximate a distal end the bonding region. Alternatively, the proximal end of intermediate tubular member 22 can be configured to form a butt joint with the distal end of proximal tubular member 20, if desired. In this manner, a polymeric sleeve can be disposed over the junction defined by the butt joint to assist securing the proximal tubular member 20 to the intermediate tubular member 22, if necessary.

A variety of bonding techniques may be utilized to secure intermediate tubular member 22 to the bonding region of proximal tubular member 20. For example, and not limitation, fusion bonding, adhesive, welding, and the like can be used.

A variety of materials can be used for proximal tubular member 20. Proximal tubular member 20 is preferably formed at least in part of a suitable metallic material, such as a metallic hypotube. For example, and not limitation, various metals can be used including stainless steel, nitinol, and other metal alloys. If stainless steel is used, preferably austenitic stainless steel is used. The metal or metal alloy is preferably MRI compatible, such as but not limited to niobium, tantalum, tungsten, or any variety of other paramagnetic metals.

Alternatively, the proximal tubular member 20 can be formed at least in part of a non-metallic material. For example and not limitation, the proximal tubular member 20 can be made of a carbon material, polymeric material, Kevlar, and reinforced materials such as carbon fiber reinforced material, glass fiber reinforced material, boron fiber reinforced material or liquid crystal reinforced material.

As noted above, the proximal tubular member 20 can be formed of a suitable polymeric material, such as PEEK or other relatively stiff polymeric material. Alternatively, proximal tubular member 20 can be formed of a composite member or formed member comprising a fabrication of different polymers or materials. For example, the composite member can be formed of an extrusion or pultrusion of different polymers, if desired. In this regard, a variety of methods for forming a multi-material or multi-layer tubular member can be utilized. For the purpose of illustration and not limitation, the proximal tubular member can be a braided polymeric member, e.g., a polymeric tube having a metal member embedded or secured to the polymer.

Alternatively, the composite member can be formed by a dip molding process, in which a mandrel is dipped into a polymer material, which is dissolved in suitable solvent, dried, and then re-dipped into another polymer material to form a multi-layered polymeric composite or formed member. As yet another alternative, the composite member or formed member can be formed by applying a second polymeric tube about a first polymeric tube, applying a shrink tubing about first and second polymeric tube assembly and heating the assembly to fuse the first and second tubular members to each other. For each process for forming the composite or formed member described above, the outer surface of the inner polymeric tube can be roughened by mechanical or chemical means to improve the bond between the inner and outer tubular members. For example, the outer surface can be roughened by mechanical means including grinding, sandblasting, or Laser-ablation, or chemical means including etching and leaching.

The composite member or formed member can also include a polymeric tubular member loaded with particles of a different polymer. For example and not limitation, a PEEK or polyimide tubular member can be loaded with PTFE particles. In this manner, the PTFE particles can be electrostatically charged such that an electrostatic force bonds the PTFE particles to the PEEK or polyimide tubular member. A polymeric outer layer, such as nylon tube, can be applied to the PTFE loaded tubular member to form a multi-material, multi-layer composite tubular member.

The use of such materials having sufficiently high compressive strength for proximal tubular member 20 is particularly advantageous to enhance pushability and provide kink resistance for rapid-exchange applications. If desired, the proximal tubular member 20 can further include a lubricious coating, such as a polytetrafluoroethylene or an HDPE coating. Alternative lubricious materials can be used, however, as known in the art. The proximal tube can also be coated with a hydrophilic or a hydrophobic coating to reduce friction, for example and not limitation, the hydrophobic coating can be silicone coating or the like, and the hydrophilic coating can be a polyvinylpyrrolidone or polyacrylamide coating.

Generally, the proximal tubular member 20 can have a length of about 100 to about 115 cm. For example and not limitation, the proximal tubular member can be configured to have an outer diameter approximately 0.70 mm and an internal diameter of about 0.52 mm. However, as known in the art, the length and dimensions of the proximal tubular member can be varied depending on the size and location of the lumen (s) to be traversed by the catheter 100. For example, the proximal tubular member can be configured to have smaller dimensions, e.g., outer diameter and internal diameter, if the catheter is used to treat vessels in the brain of a patient.

Intermediate tubular member includes a distal end region 22b, and preferably further includes lumen 22c defined between distal end region 22b and proximal end region 22a. As previously mentioned, proximal end region 22a is secured to at least a portion of proximal tubular member 20, preferably at a bonding region defined by a roughened outer surface. Lumen 22c is thus in fluid communication with lumen 20c.

A variety of materials can be used for intermediate tubular member 22. For example, intermediate tubular member 22 can be made from any suitable polymer material such as polyamide, PEEK, PEBAX®, PTFE, PVDF, polyimide, polyethylene, polyester, polyurethane, or liquid crystal polymers of various suitable densities. As a further exemplary alternative, intermediate tubular member 22 can be a composite member or formed member comprising a fabrication of several different materials. For example and as described above in detail, the composite or formed member can be made by extrusion or pultrusion of different polymers, if desired. Alternatively, the composite member can be formed by dip molding, applying a first polymeric tubing within a second tubular member and fusing the assembly, or by a loading the polymer tubular member with particles of a different polymer, e.g., PEEK or polyimide tubular member loaded with PTFE particles, as described above. As yet another alternative, the intermediate tubular member can be formed from a fiber-reinforced material, such as fiber-reinforced resin material, e.g., carbon, glass, aramid, boron, or a liquid crystal reinforced material.

The dimensions of the intermediate tubular member 22 will depend upon the intended application. For example, for a cardiovascular catheter, the intermediate tubular member 22 can have a length of at least approximately 10 cm, although a greater length can be used to accommodate an overlap joint with the proximal tubular member 20. For example, and not limitation, the intermediate tubular member can have an outer diameter of approximately 0.85 mm and an inner diameter of approximately 0.70 mm. However, as will be recognized in the art, the intermediate tubular member 22 can be configured with alternate lengths and dimensions, if desired.

In further accordance the invention, and as demonstrated in FIGS. 1 and 2, catheter 100 can further include a distal tubular member 24. Distal tubular member 24 has a proximal end region 24a, a distal end region 24b, and lumen 24c therebetween, and extends distally from intermediate tubular member 22 to distal section 106. The distal shaft lumen 24c is in fluid communication with lumen 22c of intermediate tubular member 22. Accordingly, an inflation lumen can be defined across a substantial length of catheter 100. If both are provided, intermediate tubular member 22 and distal tubular member 24 together thus define the intermediate section 104 of the catheter 100.

As shown in each of FIGS. 1, 8, and 9, a proximal end region 24a of distal tubular member 24 can be secured to at least a portion of distal region 22b of intermediate tubular member 22, as well as to at least a portion of a guidewire tube 30.

A variety of materials and dimensions can be used for distal tubular member 24. Indeed, if both an intermediate tubular member and a distal tubular member are provided, the two members can be formed of the same material and substantially the same cross section dimensions for uniform stiffness and flexibility, or even formed together as a single piece. Alternatively, the distal tubular member 24 can be formed of a different material and/or dimensions to vary flexibility along the length of the catheter. For example, distal tubular member 24 can be made from any suitable polymer material such as polyamide, PEEK, PTFE, PVDF, PEBAX®, polyimide, polyester, polyurethane, liquid crystal polymer, or polyethylene of various suitable densities. As a further exemplary alternative, distal tubular member 24 can be a composite member or formed member comprising a fabrication of several different materials, such as a co-extrusion or pultrusion of different polymers. Alternatively, the composite or formed member can be made by the dip molding process, polymer loading process, or by fusing first and second tubular members to each other, as described in detail above. Alternatively, the distal tubular member can be a fiber-reinforced material such as fiber-reinforced resin material, e.g., carbon, glass, aramid, or boron, or liquid crystal reinforced material.

The dimensions of distal tubular member 24 will depend upon the intended application. For example, for a cardiovascular catheter, the distal tubular member 24 can have a length of approximately 10 to 30 cm, and preferably has a length of approximately 21 to 23 cm. For example, and not limitation, the distal tubular member can have an outer diameter of at least approximately 0.80 mm and an inner diameter of at least approximately 0.68 mm. However, as will be recognized in the art, the distal tubular member 24 can be configured with alternate lengths and dimensions, if desired.

In an alternate construction, catheter 100 can have proximal tubular member 20 extend distally from adapter 110 directly to distal tubular member 24. By way of further example, distal tubular member 24 of catheter 100 can be attached directly to the proximal tubular member 20 without an intervening intermediate section 22, such that distal tubular member 24 has a proximal region secured to the bonding region of proximal tubular member 20. In this manner, the proximal region 24a of distal tubular member 24 can be in an overlapping configuration with the distal region 20b of proximal tubular member 20 to define an overlapping region. Preferably, the overlapping region has a length of approximately 10 cm. Such a device can further improve pushability of catheter 100 and prevent kinking.

In accordance with another aspect of the invention, the elongate main body of the catheter 100 can include a feature for performing a diagnostic, an interventional, or a therapeutic procedure or treatment. Preferably, although not necessarily, such a feature is disposed at least partially at the distal section 106 of the catheter 100. For example, and for purposes of illustration and not limitation, as embodied herein and as depicted in FIG. 1, the elongate main body can further include an inflatable member 114 disposed along a length of the catheter 100. The inflatable member has a proximal end 114a, a distal end 114b, and an inflation chamber 114c bounded by a surface of inflatable member 114. Inflatable member 114 can be made from a variety of materials. For purpose of illustration and not limitation, inflatable member 114 can be made from a polyether block amide ("PEBA"), polyamide, polyurethane, PET, PE, PTFE, polyester, composite materials, or a variety of other materials, including blends. Alternatively, the inflatable member can be made from a polyhydroxyalkanoate including but not limited to poly-4-hydroxybutyrate, available from Tepha Inc., Cambridge, Mass.

Inflatable member 114 can be formed from a variety of methods. In accordance with one aspect of the invention, a coneless inflatable member is provided. In this manner, the inflatable member is formed from a thin walled tubular member having a proximal end and a distal end. The thin walled tubular member is placed about the distal body portion. Each of the proximal and distal ends of the thin walled tubular member is compressed onto the outer diameter of the distal body portion. In this manner, an Iris lens, a suture, a metal (with or without a non-stick coating) band, wire, and the like can be utilized to wrap around each of the proximal and distal ends of the thin tubular member and compress the proximal and distal ends onto the distal body portion.

Optionally, the thin walled tubular member can be folded before the compression step described above. For example and not limitation, the thin walled tubular member can include 2 to 10 folds. The proximal and distal ends of the thin walled tubular member can be secured to the distal tubular member 24 of the catheter by a variety of suitable bonding techniques, such as adhesive, fusion, or preferably by welding. including but not limited to mechanical welding, laser welding, ultrasound welding, friction welding, heat welding, including light energy, RF energy, or any other suitable method known in the art. Thus, if inflatable member 114 is made of nylon, it is advantageous for distal body portion 24 to be made of a material compatible for a welded or fusion bond therebetween. For the purpose of illustration and not limitation, the inflatable member can be welded to the distal body portion using light energy, adhesive, or heat welding.

In accordance with a further aspect of the invention, an inflatable member having a tapered profile is provided. The tapered profile is achieved by a process during which a recess is defined at a targeted site of a tubular member prior to formation of the balloon therefrom. In this regard, a material removing device removes a predetermined quantity of material to define the recess. The balloon having a tapered profile is formed from the tubular member. The balloon having a tapered profile has benefits such as enhanced performance during advancement and retraction of the catheter in the vasculature of a patient, as well as enhanced maneuverability.

Figure 32A:
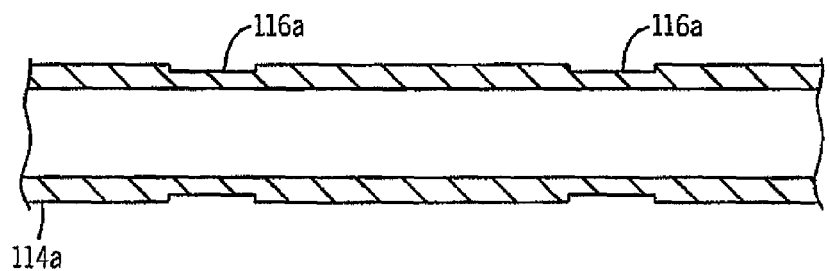
FIG. 32A schematically depicts a tubular member having a recess defined by a quantity of removed material from the tubular member.
Figure 32B:
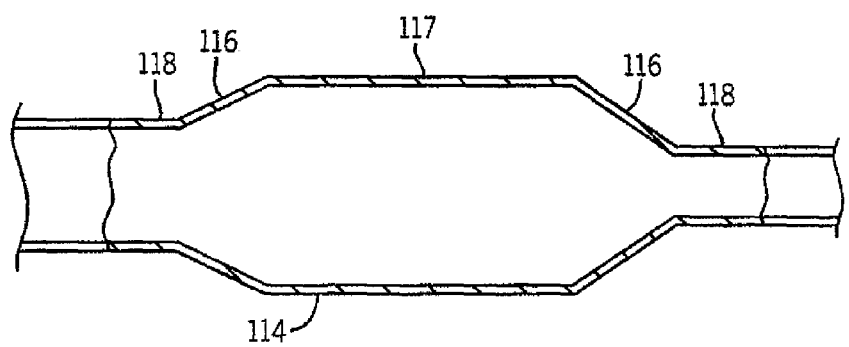
FIG. 32B schematically depicts an inflatable member formed from the tubular member of FIG. 32A.

As schematically depicted in FIG. 32A and embodied herein, at least one recess 116a is defined by the removal of a predetermined amount of material from a targeted site of a tubular member 114a. The at least one recess 116a has a length, depth, and pitch. The targeted site on the tubular member can be predetermined to correspond to any portion of the balloon formed from the tubular member. For example and not limitation, the targeted site can be disposed at a proximal, distal, or central portion of the tubular member 114a. Further, the targeted site can correspond to at least one portion of the balloon including the cone portions, waist portions, and or working portion 117 of the balloon, if desired. In this manner, the predetermined site and/or the length, depth and pitch of the recess 116a to be defined can be varied such that the target site and the configuration of the recess 116a corresponds to the cone portion 116, waist portion 118 or alternatively or in combination of the balloon 114 formed from tubular member 114a, as depicted in FIGS. 32A and 32B.

As shown and depicted in FIG. 32A, first and second recesses 116a correspond to the proximal cone portion and the distal cone portion, respectively. In this regard, the target sites for the first and second recesses 116a defined in tubular member 114a, which correspond to the proximal and distal cone portions 116 of balloon 114 are mathematically determinable by basic principles of trigonometry, as would be appreciated by one skilled in the art. For example and not limitation, to determine the target site of the tubular member, a template can be used to apply demarcations on a starting tube. The starting tube can then be processed to form a balloon. The position of certain portions of the balloon, e.g., cone portion, skirt portion and/or working portion, is determined relative to the demarcations. The demarcations that correspond to the portion of the tube at which a tapered or thinned profile is desired provides a benchmark for tubular member 114a. This procedure can be used to determine the target site for balloons of various sizes, as would be appreciated in the art. Thus, the target site of the tubular member 114a which corresponds to the portion of a balloon to be tapered or thinned can be predetermined. In this regard, material can be removed from the targeted site to form the recess 116a prior to forming the inflatable member 114. Accordingly, balloon having a tapered profile is provided. One advantage of removing material from the tubular member as opposed to removing material after the balloon is formed is that waste material is minimized. Furthermore, removing material from the balloon after it is formed often leads to unwanted changes in polymer morphology, for example stiffer cone sections due to the crystallinity of the polymer, and alterations in the orientation of the polymer chains. As the degree of crystallinity of the polymer increases, the material increases in stiffness and brittleness. Such changes in the polymer morphology are undesirable and lead to a higher profile and reduced burst pressure. Thus, it is advantageous to provide a process in which material is removed from the tubular member prior to formation of the balloon. In this manner, crystallite formation is broken down during the heating and drawing of the tubular member to form the balloon 114 thus providing a more uniform and flexible material.

In one preferred embodiment, the material is removed from the tubular member 114a by laser ablation techniques, micromachining techniques, or a combination of such techniques. Advantageously, laser ablation techniques and micro machining techniques have high tolerance, quality and reproducibility over other removal processes known in the art. For the purpose of illustration and not limitation, a source laser such as an Eximer or "Excited Dimmer" type laser could be used. However, it will be apparent to those skilled in the art that other techniques of material removal could additionally or alternatively be employed such as, but not limited, to precision grinding techniques, cutting techniques, and the like.

Further, it will be appreciated by one skilled in the art that the length, depth and pitch of the recess 116a defined by the removed material from the tubular member can be varied to provide desired wall thicknesses at any portion of the tubular member and resultant inflatable member 114, as well as desired performance characteristics of the inflatable member formed from the tubular member.

In accordance with a further aspect of the invention, catheter can include a first guidewire lumen defined along a length of the catheter and a second lumen defined proximal to the first guidewire lumen along a length of elongate main body of catheter.

For example, and with reference to FIG. 1, catheter 100 is provided with a first guidewire tube 32 having a first guidewire lumen defined therethrough. The first guidewire lumen 32c accordingly can be provided with a proximal guidewire port 32a and a distal guidewire port 32b in fluid communication therewith. Similarly, the catheter 100 is provided with a second guidewire tube 30 having a second guidewire lumen defined therethrough. The second guidewire lumen 30c accordingly can be provided with a proximal guidewire port 30a and a distal guidewire port 30b in fluid communication therewith.

As embodied herein, the first guidewire lumen 32c is disposed along the distal section 106 of the catheter. For example, if an inflatable member 114 is provided, first guidewire lumen 32c extends through the inflatable member with the distal guidewire port 32b located distal the inflatable member and the proximal guidewire lumen located proximal the inflatable member. In a preferred embodiment, inflatable member 114 is positioned on the elongate main body of catheter 100 equidistant between the proximal guidewire port 32a and distal guidewire port 32b, or the distal end of the tip 70, if provided. However, inflatable member 114 can also be placed closer to one port or the other, if desired.

Furthermore, and as embodied herein, the second guidewire lumen 30c is disposed proximal to and spaced from first guidewire lumen 32c. That is, distal guidewire port 30b of second guidewire lumen 30c is spaced proximal from proximal guidewire port 32a of first guidewire lumen 32c. A guidewire inserted proximally distal guidewire port 32b therefore will exit the catheter at proximal port 32a. As illustrated in FIG. 1, proximal guidewire port 32a of first guidewire lumen 32c is preferably axially aligned with distal guidewire port 30b of second guidewire lumen 30c. Advantageously, and as embodied herein and depicted in FIGS. 8 and 9, this arrangement provides an operator with an option to feed guide wire 60 solely through lumen 32c of first guidewire tube 32, as mentioned above and schematically shown in FIG. 8, or alternatively, feed guidewire 60 through each of first guidewire lumen 32c and second guidewire lumen 30c of second guidewire tube 30, as shown in FIG. 9.

Figure 6:
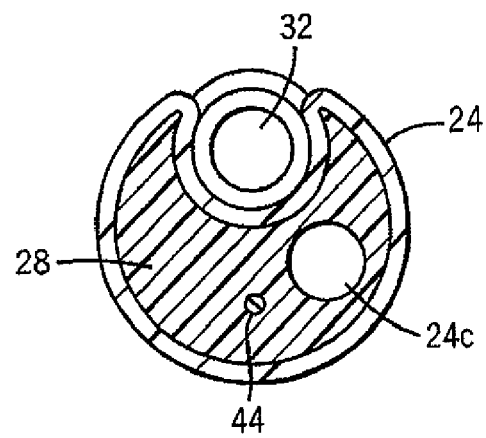
FIG. 6 is a cross sectional view at line 6-6 of the catheter of FIG. 1 in accordance with the present invention.

In a preferred embodiment of the invention, at least the first guidewire lumen 30c is defined by a first guidewire tube 30. The first guidewire tube 30 embodied herein, is joined at its distal end region to the distal end of inflatable member 114 by conventional bonding techniques as depicted in FIG. 1. To anchor the proximal end region of first guidewire tube 32, and in accordance with another aspect of the invention, a circumferential slit is formed in the wall of distal tubular member 24. The wall on the proximal side of the circumferential slit is urged inward, such that the proximal end region 32a of first guidewire tube 32 extends through the slit with the wall of the distal tubular member substantially surrounding the first guidewire tube 32 as depicted in FIG. 6. A reinforcement filler or tube can be provided proximate the slit to anchor and strengthen the joint between the tubular members.

The second guidewire lumen can be formed or defined by a separate tubular member disposed along a length of distal tubular member 24, or can be defined by the distal tubular member 24, itself, as described further below. If formed of a separate tubular member, the second guidewire tube can be anchored at its distal end region to distal tubular member 24 in a manner similar to that of the proximal end region of the first guidewire tube.

Particularly, and as depicted in FIG. 1 in accordance with either aspect of the invention, distal tubular member 24 further includes gap 24d along its length. Gap 24d is in fluid communication with the exterior of catheter 100. For purpose of illustration and not limitation, gap 24d can be constructed by placing two circumferential slits through the wall of distal tubular member 24 to define a flap region. The flap region is depressed toward lumen 24c of distal tubular member 24. As best viewed from FIG. 6, which illustrates a cross section of a portion of catheter 100 at gap 24d, the depressed flap portion is depressed within lumen 24c such that a portion of the wall of distal tubular member 24 has a concave shape. Further, and as schematically shown in FIG. 1, the depressed flap region of distal tubular member 24 is disposed between a first guidewire tube 32 and a second guidewire tube 30. As schematically shown in FIG. 1, second guidewire tube 30 is disposed proximal to gap 24d and first guidewire tube 32 is disposed distal to gap 24d. Advantageously, gap 24d allows fluid communication between the exterior of catheter 100 and both the distal guidewire port 30b of second guidewire lumen 30c, and the proximal guidewire port 32a of first guidewire lumen 32c. Further, and as schematically depicted in FIG. 8, gap 24d provides an exit for a guidewire 60 disposed in the first guidewire lumen 32c, if desired.

As previously stated, a filler material or reinforcement tube 28 can be placed below the gap 24d to strengthen the region proximate the joints. If provided, a mandrel can be inserted during fusion of the members to ensure an inflation lumen is maintained. Additionally, if a stiffening element is provided in the lumen of the tubular member, the filler material provides added material to the sidewall of the tubular member so that the stiffening member does not disrupt the sidewall of the tubular member when the catheter is manipulated during use or during assembly.

The proximal end region of the second guidewire tube, if provided as a separate member, can be secured or anchored in a variety of different manners. For example, and as embodied herein, the proximal end region of second guidewire tube 30 can be secured between the distal end region 22b of intermediate tubular member 22 and the proximal end region 24a of distal tubular member 24 as depicted in FIG. 1. In a preferred embodiment, the distal end region 22b of intermediate tubular member 22, as depicted in FIG. 1, can further include a longitudinal recess such that at least a portion of second guidewire tube 30 is nested within the longitudinal recess of the intermediate tubular member 22. For the purpose of illustration and not limitation, the longitudinal recess can be formed by necking down a distal region of the intermediate tubular member 22 or forming a dimple in of the intermediate tubular member.

With the second guidewire tube 30 positioned between the overlapping interface of the intermediate tubular member 22 and the distal tubular member 24, the structure can be fused together to form a joint therebetween. If desired, a filler material or reinforcement tube 26 can be disposed proximate the joint as depicted in FIG. 1. Preferably, a mandrel is located temporarily across the joint when the structure is fused together to define an inflation lumen 22 therethrough, as depicted in FIG. 3.

Alternate constructions for the second guidewire lumen, and the corresponding region, are describe further below.

The material of construction and dimensions for the guidewire lumens will depend upon the intended application. For example, for a cardiovascular catheter, each of the first and second guidewire lumens can be constructed from any suitable polymer such as nylon, PEEK, HDPE, polyimide, PTFE, or PTFE loaded polymer, e.g., polyimide, polyurethane, polyester, liquid crystal polymer, and the like, including blends or composites thereof. Further, each of the lumens can be made of one or more extruded or pultruded materials, including multilayered co-extrusions or pultrusions, or monolayered material, as discussed below. The guidewire lumens can also be made from a dip molding process or applying a first polymeric tubing within a second tubular member and fusing the assembly together.

The first guidewire lumen can have a length of at least approximately 1 cm, and second guidewire lumen can have a length of at least approximately 17 cm.

Catheter 100 can be configured to have proximal guidewire port 30a approximately 10 to 30 cm, and preferably about 20 to 30 cm, proximal to distal tip 70 of catheter 100. Accordingly, catheter 100 can be configured such that guidewire 60 can be disposed through first guidewire tube 32 and exits catheter body at guidewire port 32a of first guidewire tube 32 and then re-enters catheter body 100 at distal port 30b of second guidewire tube 30. Guidewire 60 extends proximally through second guidewire lumen 32c to proximal port 30a.

Alternatively, guidewire 60 can be disposed through guidewire tube 32 and exit catheter 100 through proximal guidewire port 32a at gap 24d. Proximal guidewire port 32a is preferably disposed near the proximal end 114a of inflatable member 114. For example and not limitation, proximal port 32a can be disposed approximately 8 cm proximal to distal tip 70. Alternatively, the proximal port 32a can be disposed at a variety of other distances from distal tip 70, depending upon the length of the inflatable member 114 or the intended application. In one preferred embodiment, the length between inflatable member 114 and proximal guidewire port 32a is substantially the same as the distance between inflatable member 114 and distal guidewire port 32b.

Generally, first guidewire tube 32 is shorter in length than second guidewire tube 30. For example and not limitation, first guidewire tube 32 can have a length of at least approximately 3 to 4 cm; although generally is dependent at least on the length of inflatable member 114. Second guidewire tube generally has a length of approximately 10 to 30 cm, and preferably about 21 to 23 cm, depending on the length of the inflatable member 114. Preferably, the outer diameter of first and second guidewire tubes, 32 and 30, respectively, are approximately 0.55 mm, and the inner diameter of first and second guidewire tubes, 32 and 30, respectively, are approximately 0.42 mm. However, it should be recognized that each of first guidewire tube 32 and second guidewire tube 30 can have any suitable length and dimension, as desired.

A variety of materials can be used to form first guidewire tube 32 and second guidewire tube 30. For example and not limitation, either first guidewire tube 32 or second guidewire tube 30 can be formed of suitable polymer material such as polyamide, PEEK, HDPE, PEBAX®, PTFE, PVDF, polyimide, polyethylene, polyester, polyurethane, or liquid crystal polymers of various suitable densities, including blends thereof.

As a further exemplary alternative, either guidewire tube 30, 32 can be formed of a composite member or formed member comprising a fabrication of several different materials. For example and as described above in detail, the composite or formed member can be made by extrusion or pultrusion of different polymers, if desired. Alternatively, the composite member can be formed by dip molding, applying a first polymeric tubing within a second tubular member and fusing the assembly, or by a loading the polymer tubular member with particles of a different polymer, e.g., PEEK or polyimide tubular member loaded with PTFE particles, as described above. Alternatively, either guidewire tube can be formed from a fiber-reinforced composite material such as fiber-reinforced resin material including but not limited to carbon reinforced material, glass reinforced material and boron reinforced material, or a liquid crystal reinforced material.

In one preferred embodiment, second guidewire tube 30 is formed of a multi-layered co-extrusion, and first guidewire tube 32 is formed of a monolayer polymeric material. For example and not limitation, second guidewire tube 30 can be formed of at least a two-layer material including an inner polymeric layer and an outer polymeric layer. Preferably, the inner layer is a lubricious material and facilitates gliding of guidewire 60 through guidewire lumen. Alternatively, the inner material can have a lubricous coating, for example, with a silicone coating.

In one preferred embodiment, the second guidewire tube is formed of an inner layer including HDPE and an outer layer including a polyamide, such as nylon. However, alternative materials can be used for either the inner layer or the outer layer as known in the art. For example, the inner layer can alternatively be formed from materials such as polyimide, PTFE, or PTFE loaded polyimide and the outer layer can be formed from materials including nylon, nylon copolymers including Pebax®, Hytrel®, polyolefin, polyurethane, and blends thereof. Alternatively, other suitable materials can be used as known in the art.

The inner layer can be secured to the outer layer by various suitable methods and structures, which depend on the particular selection of the inner layer material and the outer layer material, as known in the art. For example, the inner layer can be secured to the outer layer by a mechanical bond, chemical bond, or other bonding means such as mechanical friction fit. For example and not limitation, a lubricious inner layer of HDPE is mechanically bonded to an outer layer of nylon.

As mentioned above, guidewire tube 32 is preferably formed of a monolayer polymeric material. As depicted in FIG. 1, distal end of inflatable member 114 is secured to first guidewire tube 32. Accordingly, the particular material selected for the first guidewire tube 32 should be compatible with the material selected for the inflatable member 114. Preferably, first guidewire tube 32 is formed of a monolayer of nylon, and inflatable member 114 is a nylon balloon, such that a fusion bond can be formed therebetween. Alternatively, the inflatable member can be adhesively bonded to the first guidewire tube. Alternatively, both members can be formed of a PEBA material. Furthermore, the first guidewire tube can be formed of a multi-layer tubular member, if desired.

In further accordance with the invention, distal tip 70 can be secured to first guidewire tube 32. As depicted, distal tip 70 is in an overlapping configuration with the distal end of first guidewire tube 32. In one embodiment, distal tip is configured to abut the distal end of inflatable member 114. Alternatively, however, distal tip 70 can be configured to overlap the distal end of inflatable member 114. Preferably, distal tip 70 is secured to the distal end of first guidewire tube by heat welding. However, other methods can be used such as using adhesives, or the like.

A variety of materials can be used to form distal tip 70. Preferably, distal tip 70 is formed of a material having a durometer less than the durometer of the distal tubular member 24. For example and not limitation, distal tip 70 can be formed of polyamides, including nylon, polyether block amide, high density polyethylene, polyurethane, polyesters, including HYTREL®. The particular selection of the material for the distal tip 70, however, is depending on the desired application of catheter 100.

As previously noted, the second guidewire lumen can be formed by a second guidewire tube or by other construction. For example, FIG. 1 depicts a catheter with second guidewire lumen 30c defined by second guidewire tube 30. The proximal guidewire port 30a is defined wholly by the proximal end region of second guidewire tube 30 due to the joint configuration previously described. In this manner, and by using a tubular member with a lubricious inner layer, placement of the catheter relative to the guidewire can be enhanced.

Figure 4A:
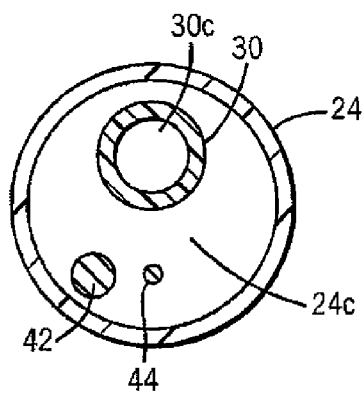
FIG. 4A is a cross sectional view at line 4-4 of the catheter of FIG. 1 in accordance with an embodiment of the present invention.

Between the proximal guidewire port 30a and the distal guidewire port 30b, the second guidewire lumen 30c can be disposed either in a coaxial relation or a side-by-side relation with the inflation lumen 24c, or even a hybrid of the two. For the purpose of illustration and not limitation, FIG. 4A depicts a cross section of a portion of catheter 100 in which second guidewire tube 30 is disposed generally coaxially within distal tubular member 24, such that inflation lumen 24c annularly surrounds guidewire tube 30 and guidewire lumen 30c.

Figure 4B:
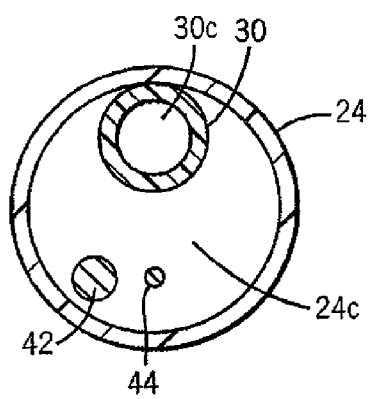
FIG. 4B is an alternate cross sectional view at line 4-4 of the catheter of FIG. 1 in accordance with an embodiment of the present invention.

Alternatively, as embodied herein, and as depicted in FIG. 4B, catheter 100 can include a modified, dual lumen configuration. That is, second guidewire tube 30 can be secured by any suitable bonding technique along all or a portion of its length to a longitudinal inner surface of distal tubular member 24. Accordingly, inflation lumen 24c surrounds only a portion of guidewire tube 30. In one preferred aspect of the invention, a light absorption welding technique of EP 1435252, the contents of which are incorporated herein by reference herein, can be used.

Figure 4C:
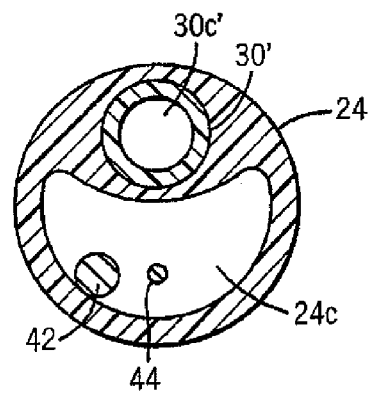
FIG. 4C is another cross sectional view at line 4-4 of the catheter of FIG. 1 in accordance with an embodiment of the present invention.
Figure 5:
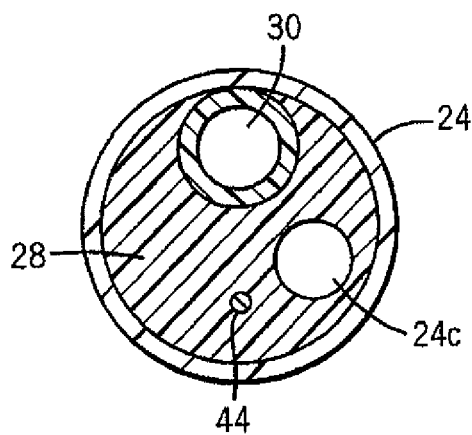
FIG. 5 is a cross sectional view at line 5-5 of the catheter of FIG. 1 in accordance with the present invention.

In yet another alternative, as embodied herein and as depicted in FIG. 4C, catheter 100 can be configured to include a conventional dual lumen configuration along at least a portion of the intermediate region 104. The term "conventional dual lumen configuration" refers to a configuration in which guidewire lumen 30c' and inflation lumen 24c are arranged generally in parallel and side-by-side relationship. Such dual lumen configurations are available as a single extrusion of suitable polymer material, such as nylon or the like. If desired, and as illustrated in FIG. 4C, second guidewire tube can further include at least a portion 30' formed of a lubricious tube or liner, such as HDPE, PTFE, PEEK or the like. As depicted in FIG. 4C, inflation lumen 24c can be configured to have a crescent or generally semi-circular shaped cross-section. Such a semi-circular shaped cross section is advantageous because it maximizes the cross sectional area of inflation passage 24c, thus minimizing flow resistance to inflate inflatable member 114.

Alternatively, the dual lumen member can be constructed by dip molding, shrink fitting, melting or fusing two or more tubular members together. For example, and not limitation, the second guidewire tube and an inflation tube can each be formed by a suitable liner. The guidewire tube liner and the inflation tube liner are arranged generally in a parallel and side-by-side relationship within a polymeric tubular member. The assembly is then heated to a temperature to cause the polymeric tubular member to melt around a substantial portion of each of the second guidewire tube liner and the inflation tube liner to secure the liners in a dual lumen configuration. A removable shrink wrap can be used to shape the outer surface of the member during the fusion process.

If the distal tubular member 24 is formed at least in part by a dual lumen extrusion or pultrusion formed member, as described above, then a number of different joint configurations can be used in accordance with the invention. For example, and as embodied herein and depicted in FIG. 10, the distal end region 22b of intermediate tubular member 22 can be provided in an overlapping configuration with the proximal end region 24a of distal tubular member 24. At least a portion of distal tubular member includes a guidewire lumen 30c and an inflation lumen 24c in a side-by-side configuration.

Figure 14A:
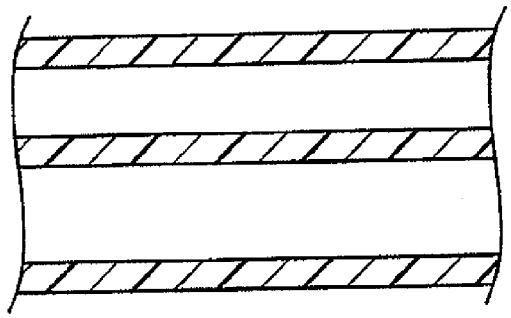
FIG. 14A to 14G is a schematic representation of a method to manufacture the catheter of FIG. 10 in accordance with the present invention.
Figure 14B:
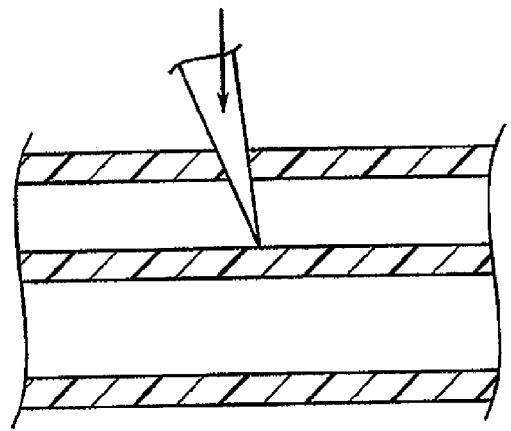
Figure 14C:
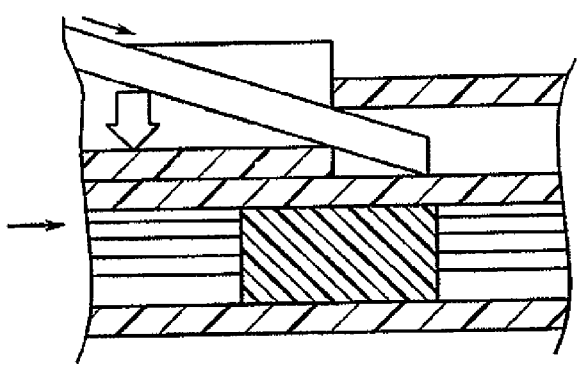

To be received within the distal end region of intermediate tubular member 22, at least the proximal end region of the dual lumen member can be collapsed, as depicted in FIGS. 14A through 14G, and in particular FIG. 14C, described further below. Alternatively, the distal end region of intermediate tubular member 22 can be received within the proximal end region of the dual lumen member, as depicted in FIGS. 17A to 17G, and particularly in FIG. 17E.

Distal tubular member 24 further includes at least one first filler material or reinforcement member 26 within the inflation lumen 24c proximate the joint between the intermediate and distal members. A cross sectional view of catheter 100 at line 11-11 of FIG. 10, as depicted in FIG. 11, demonstrates that second stiffening member 42, as described further below, can be embedded in material of reinforcement member 26 after fusion to form a joint therebetween. As depicted in the cross sectional view of catheter 100 in FIG. 12, the dual lumen member transitions distally to define a portion of the catheter 100 that includes guidewire lumen 30c and inflation lumen 24c. To strengthen the joint, filler material or a reinforcement tube is provided, and a removable mandrel is disposed prior to fusion such that inflation lumen 24c having a circular or crescent-shaped cross section is formed, as demonstrated in FIG. 12. Ultimately, the dual lumen member transitions to a conventional configuration with guidewire lumen 30c and inflation lumen 24c in a side-by-side relationship with inflation lumen 24c having a crescent or substantially semi-circular cross section, as demonstrated in FIG. 13.

For the purpose of illustration and not limitation, the catheter 100 of FIG. 10 can be manufactured by the steps schematically and sequentially depicted in FIGS. 14A to 14G.

Figure 14D:
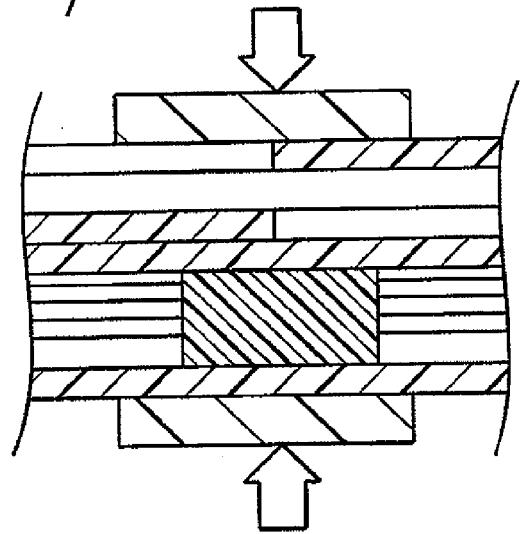

As demonstrated in FIGS. 14A and 14B, a partial circumferential cut 118 is made in a dual lumen member 24 to define proximal guidewire port 30a. A series of removable mandrels 120 are used to maintain the lumens and port of the dual lumen structure, as desired, during the heating and fusion steps, as depicted in the Figures. For the purpose of illustration, a removable mandrel 120 can be inserted into the defined proximal guidewire port 30a and along guidewire lumen 30c. Another removable mandrel 120 can be inserted into the inflation lumen, as depicted in FIG. 14C. The proximal region of the dual lumen member 24 can be collapsed to configure the opening of proximal guidewire port 30a, as depicted in FIG. 14C. A removable shrink tubing 124 can be applied to the dual lumen member 24. The assembly can be heated to form proximal guidewire port 30a and to connect the collapsed proximal end of dual lumen member 24 to the guidewire lumen sidewall, as depicted in FIG. 14D.

Figure 14E:
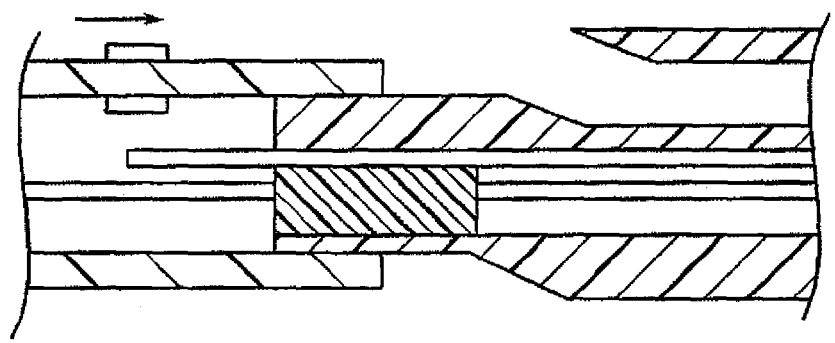
Figure 14F:
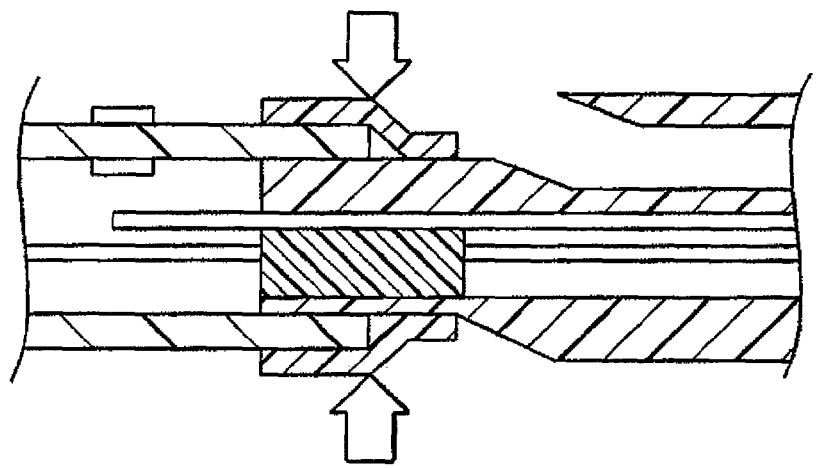

As previously described, and as shown in FIGS. 14C and 14F, a reinforcement member 26 can be inserted along the elongate main body to secure the stiffening member within the lumen of the elongate main body. Additionally, a mandrel is provided along the elongate main body to define at least a portion of the inflation lumen through the reinforcement member 26.

Figure 14G:
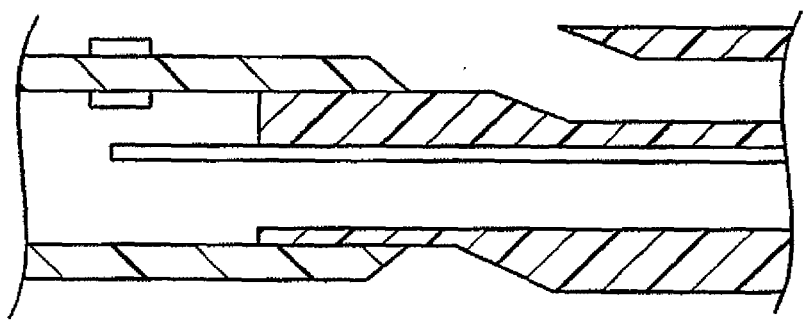

As depicted in FIGS. 14E and 14F, the intermediate tubular member 22 can be secured to the proximal end of the dual lumen tubular member by applying a removable shrink tube 124 and appropriate application of heat to fuse the members together. FIG. 14G depicts the catheter 100 including formed proximal guidewire port and joint configuration.

Figure 17A:
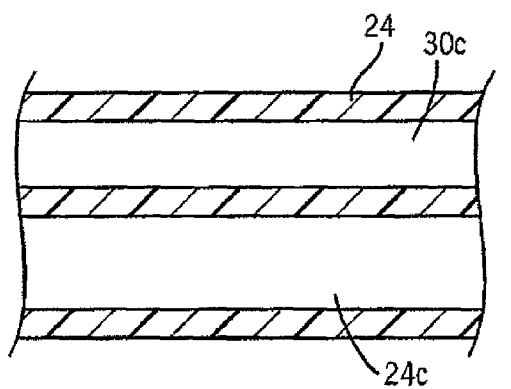
FIG. 17A to FIG. 17 G is a schematic representation of a method to manufacture the catheter of FIG. 15 in accordance with the present invention.
Figure 17B:
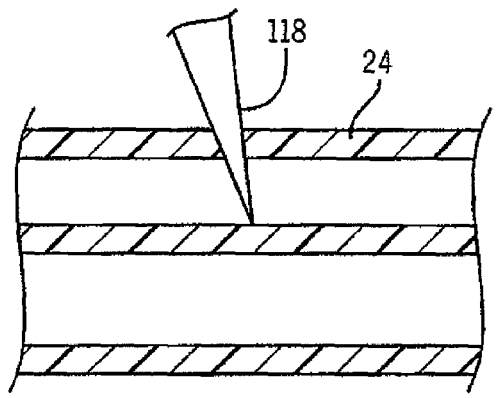
Figure 17C:
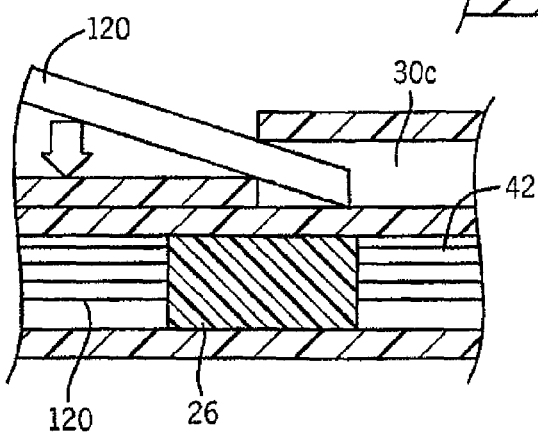
Figure 17D:
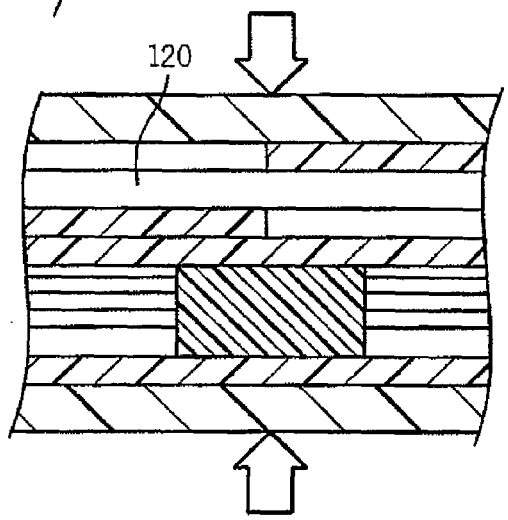
Figure 17E:
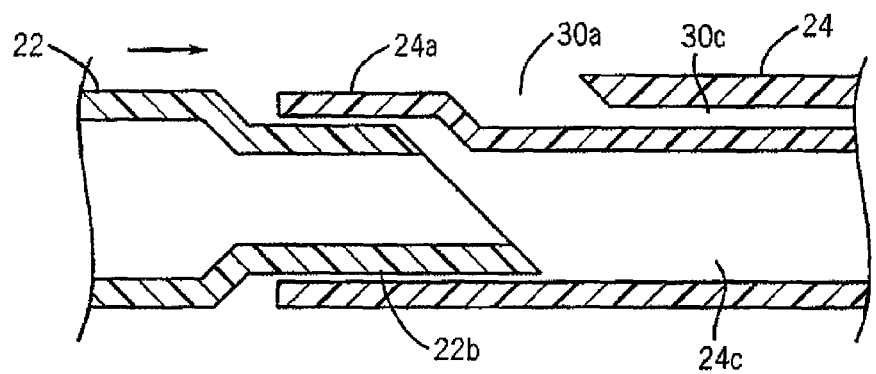
Figure 17F:
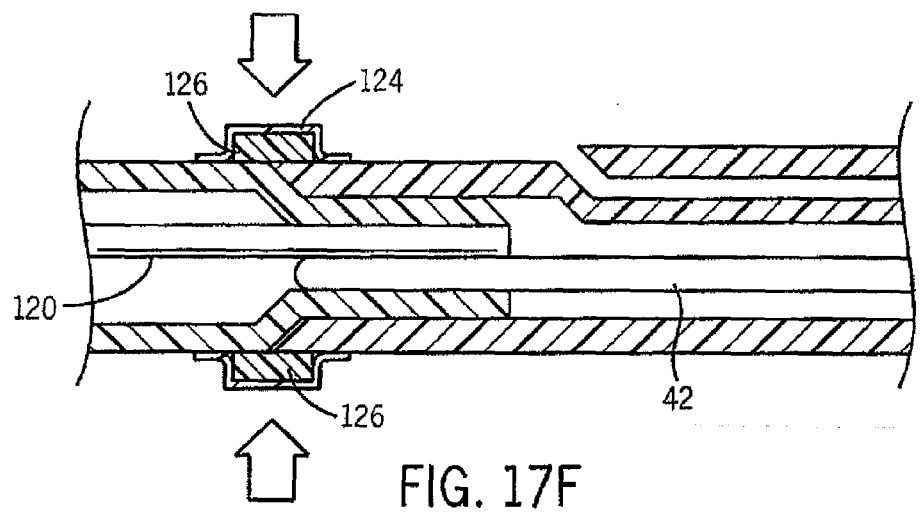
Figure 17G:
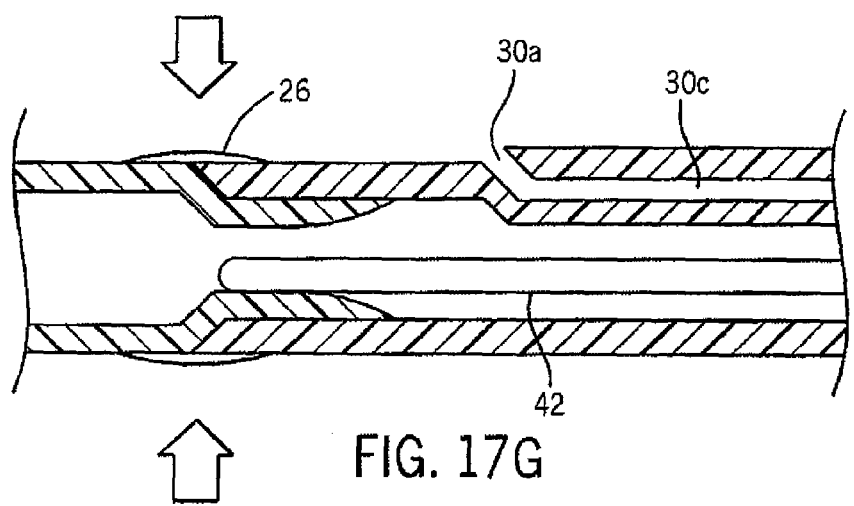

Alternatively, as demonstrated in FIG. 16 and FIGS. 17A to 17G, and in particular FIG. 17E, the distal end region 22b of intermediate tubular member 22 having reduced cross dimension can be received and secured within proximal end region 24a of distal tubular member 24. To accomplish this configuration, and in accordance with the another aspect of the invention, the assembly depicted in FIG. 15 can be manufactured by the steps schematically and sequentially depicted in FIGS. 17A to 17G. Particularly, and in lieu of or in addition to disposing reinforcement members 26 within the lumen at the joint, the assembly, as depicted in FIG. 15, includes at least one first reinforcement member 26 placed about at least one of distal tubular member 24 or intermediate tubular member 22 as viewed in FIG. 16 and FIG. 17F. As illustrated, the distal member and the intermediate member can be secured by applying a removable heat shrink tube 124 and appropriate heat to fuse the members together. FIG. 17G depicts the catheter 100 including the alternative formed proximal guidewire port and joint configuration with mandrel 120 removed.

Although reference has been made to alternative methods and configurations for joining the proximal end of the dual lumen member to the intermediate tube, such methods and configurations also can be used for joining the distal end of the dual lumen member to an adjacent tubular member as desired. For example, the distal end of the dual lumen member can be attached to the first guidewire lumen and either an outer distal tube member or directly to the balloon using the methods similar to that of FIGS. 14A-14G or FIG. 16, so as to define a configuration similar to that depicted in FIGS. 5-6 at region 28a.

Furthermore, inflation lumen 24c and/or guidewire lumen 30c can be configured to have any of a variety of cross-sectional shapes. For example and not limitation, the cross-sectional shape inflation lumen 24c can be substantially elliptical, substantially rectangular, or be defined by a polygon (e.g., a hexagon), among others.

Figure 7:
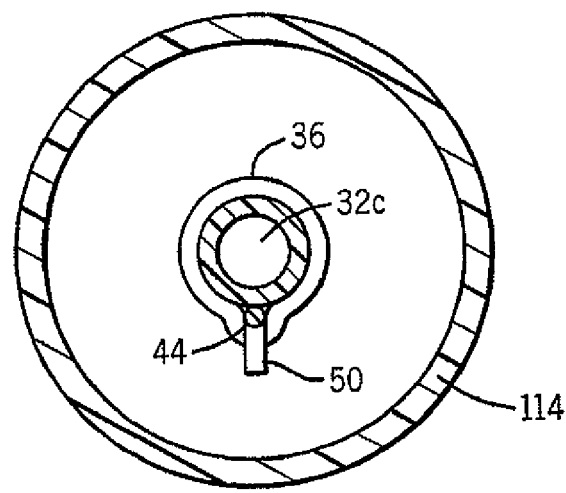
FIG. 7 is a cross-sectional view at line 7-7 of the catheter of FIG. 1 in accordance with the present invention.

In further accordance with a further aspect of the invention, and as noted above, first guidewire tube 32, as illustrated in FIG. 7, can be arranged in a coaxial arrangement at least with a portion of inflatable member 114. Thus, in accordance with a further aspect of the invention, catheter 100 can be configured to include a transition along at least a portion of its length. In particular, catheter 100 can have a first segment along its length in which second guidewire tube 30 is arranged in a side-by-side configuration or a modified, side-by-side configuration, and a second segment in which first guidewire tube 32 is arranged in a coaxial configuration. Accordingly, it is an aspect of the present invention to include a catheter 100 having a transition along at least a portion of its length.

Further in accordance with another aspect of the invention, the second guidewire lumen can be configured to be entirely in a coaxial relationship with inflation lumen along the length therebetween the proximal guidewire port 30a and the distal guidewire port 30b, or entirely in a side-by-side relation therebetween, or a combination of the two. That is, a portion of the length of the distal tubular member 24 can be formed of a dual lumen member, as described, with an additional portion of the distal tubular member formed of an outer tubular member and an inner tubular member in coaxial relationship, such that at least the inner tubular member is joined in fluid communication with one of the lumens of the dual lumen member.

In accordance with a further aspect of the invention, the catheter can include an elongate main body having one or more stiffening members. The term "stiffening member" can include a filament, strand, wire, coil, tubular member, or other member to increase the stiffness of a section of the catheter elongate main body. Preferably, however, the stiffening member is a wire member.

In a preferred embodiment, and in accordance with an additional aspect of the invention, the catheter includes an elongate main body and a plurality of stiffening members disposed along a length of the elongate main body. The plurality of stiffening members includes a first stiffening member and a second stiffening member disposed in an overlapping and spaced relationship. Particularly, and as embodied herein and schematically depicted in FIG. 1, catheter 100 can include first, second, and third stiffening members, 40, 42, and 44, respectively.

First stiffening member 40 has a proximal end 40a, a distal end 40b, and a midpoint therebetween. The midpoint is preferably equidistant from the proximal end and the distal end of the stiffening member. In one embodiment, as shown in FIG. 1, first stiffening member 40 is disposed along the proximal portion 102 of the elongate main body and has a proximal end secured to adapter 110 and a length sufficient extend distally through and beyond lumen 20c of proximal tubular member 20. The distal end of first stiffening member is freely floating or unattached to the catheter main body.

First stiffening member 40 can be secured to the adapter by adhesive, welding, or alternatively, can be embedded into the adapter during an injection molding process. Alternatively, and as schematically depicted in FIG. 2, first stiffening member 40 can be secured to the elongate main catheter body of catheter 100 such that at least a proximal portion of the stiffening member 40 is freely-floating or unsecured within the proximal tubular member 20. For example and not limitation, and intermediate location, such as the midpoint, or the distal end of first stiffening member 40 can be secured to intermediate tubular member 22 or another member of the main body. In yet another alternative, first stiffening member 40 can have at least one of the proximal end or distal end secured to its proximal tubular member 20. For example and not limitation, if the proximal tubular member is formed of metal, first stiffening member 40 can be welded, brazed, or soldered at or near the distal end of proximal tubular member 20 or to a region proximal to the distal end of proximal tubular member 20.

Figure 28:
FIG. 28 depicts a stiffening member in accordance with the invention.

First stiffening member 40 can include a taper or stepped region of increasing or decreasing cross dimension. For example and not limitation, FIG. 1 demonstrates that first stiffening member is configured to have a stepped region of increasing cross dimension with the transition located within the proximal tubular member 20. As depicted, the stepped region of increasing cross dimension can be defined by an extension member 60 secured to the distal region 40b of the first stiffening member. However, first stiffening member 40 can be configured to include a taper, if desired, which extends along a portion of the entire length of the member, as depicted in FIG. 18E and FIG. 28. Additionally, first stiffening member can be configured to have a uniform cross section which changes from a circular configuration to a semi-circular configuration, as depicted in FIG. 28.

First stiffening member can have a length of approximately 110 to about 125 cm and include a first section having an outer diameter of about 0.1 mm, a second section having an outer diameter of 0.2 mm, and a third section having an outer diameter of about 0.3 mm. However, it should be recognized that other lengths and dimensions can be used. In a preferred embodiment, the first stiffening member has a length disposed in the proximal tubular lumen 20c such that the transition from a larger outer diameter to a smaller outer diameter is proximal to the distal end region 20b of proximal tubular member 20.

FIG. 1 further depicts second stiffening member 42 having a proximal end 42a and a distal end 42b and a length therebetween. Second stiffening member 42 can be secured to at least one region of the elongate main body of catheter 100. Alternatively, and as depicted in FIG. 18B, each of first and second stiffening member can be secured to a support member 92 disposed along the elongate main body.

Figure 18A:
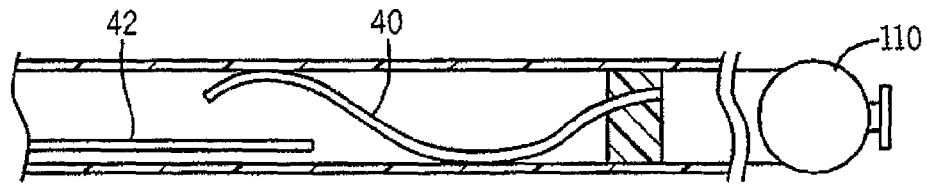
FIG. 18A is a schematic side view of a representative embodiment of a catheter having a plurality of stiffening members.
Figure 18B:
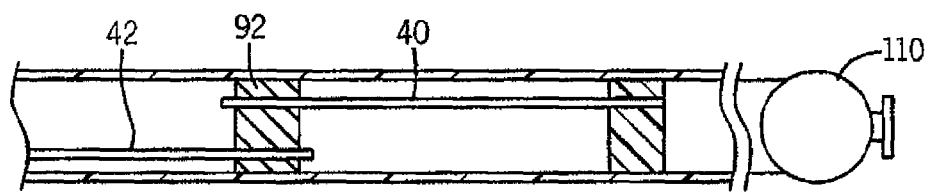
FIG. 18B is a schematic side view of an alternative embodiment of a catheter having a plurality of stiffening members.
Figure 18C:
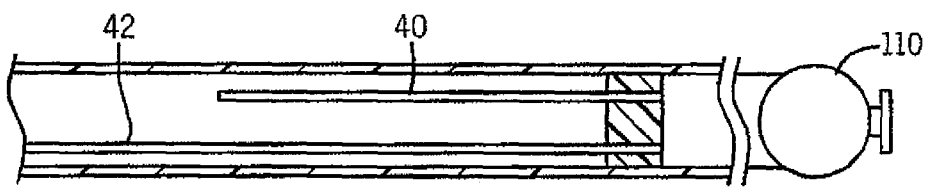
FIG. 18C is a schematic side view of an alternative embodiment of a catheter having a plurality of stiffening members in accordance with the present invention.
Figure 18D:
FIG. 18D is a schematic side view of an alternative embodiment of a catheter having a plurality of stiffening members in accordance with the present invention.
Figure 18E:
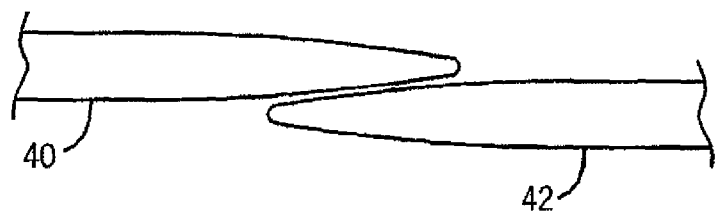
FIG. 18E is a schematic side view of a first stiffening member and a second stiffening member, each having a taper in accordance with the present invention.
Figure 18F:
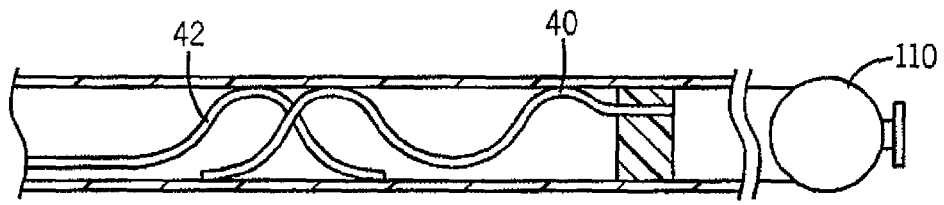
FIG. 18F is a schematic side view of an alternative embodiment of a catheter having a plurality of stiffening members in accordance with the present invention.
Figure 18G:
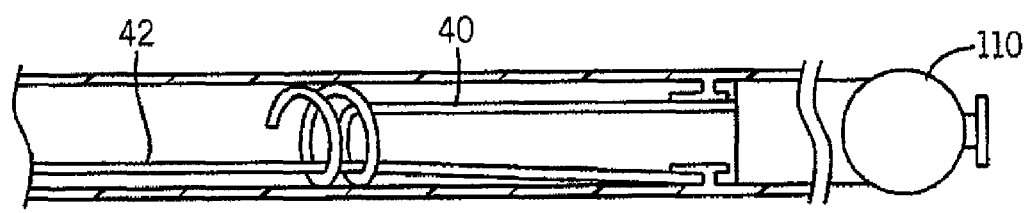
FIG. 18G is a is a schematic side view of an alternative embodiment of a catheter having a plurality of stiffening members in accordance with the present invention.
Figure 18H:
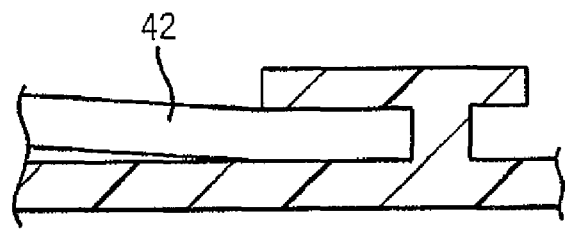
FIG. 18H is a schematic side view of a stiffening member secured to the elongate main body of a catheter in accordance with the invention.
Figure 20:
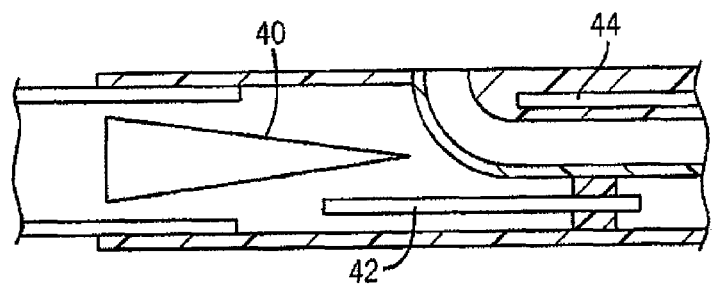
FIG. 20 is a schematic side view of a catheter having a plurality of stiffening members disposed in an overlapping and spaced relationship in accordance with the present invention.
Figure 21:
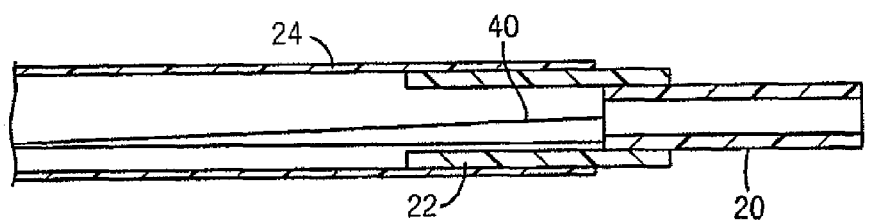
FIG. 21 is a schematic side view of a catheter having at least one stiffening member secured to the elongate main body in accordance with the present invention.

As yet another alternative, catheter 100 can include an engagement member to define a longitudinal cavity or space between the engagement member and the inner surface of the elongate main body to engage the stiffening member in the longitudinal cavity or space, as depicted in FIG. 18H.

For example, and not limitation, second stiffening member 42 can be disposed in inflation lumen 22c and secured at an intermediate location to an inner surface of intermediate tubular member 22. In this regard, the distal end 42b and the proximal end 42a of second stiffening member 42 can each be configured to freely-float within the lumen 22c. As another illustrative example, second stiffening member 42 can be secured at least one of its proximal end or its distal end to a region of the elongate main body of catheter 100. Preferably, and as illustrated in FIG. 1, second stiffening member 42 is secured within reinforcement member 26. Reinforcement member 26 is preferably a polymeric member including but not limited to a tubular member or a filler material. The added material 26 can fuse into the sidewall of the elongate main body when heated or melted and prevent the stiffening member from disrupting the sidewall of the catheter.

Preferably, as embodied herein and depicted in FIG. 1, second stiffening member 42 is in an overlapping configuration with a portion of first stiffening member 40. That is, the distal end 40b of first stiffening member 40 preferably extends distally beyond the proximal end 42a of second stiffening member 42. More preferably, the stiffening members are in non-connected relationship. As illustrated in FIG. 18E, first stiffening member 40 can be configured to include a distal taper and second stiffening member can be configured to include a proximal taper. Further, the overlapping configuration can include the distal tapered area of the first stiffening member located along a length corresponding to the proximal tapered area of the second stiffening member.

Catheter 100 can include a third stiffening member 44, as illustrated in FIG. 1. Third stiffening member 44 has a body including a proximal end 44a, a distal end 44b, and a length therebetween. As demonstrated in FIG. 1, can best be viewed in FIGS. 4A, 4B, and 4C, third stiffening member 44 can be configured in an overlapping configuration with a portion of second stiffening member 42 and can extend distally to a region near or into inflatable member 114.

Third stiffening member 44 can be secured to at least one region of the elongate main body of catheter 100. For example, and not limitation, third stiffening member 44 can be disposed in inflation lumen 24c and secured at an intermediate location to an inner surface of distal tubular member 24. In this regard, the distal end 44b and the proximal end 44a of third stiffening member 44 can be secured at least one of its proximal end or its distal end to a region of the elongate main body of catheter 100. Preferably, and as illustrated in FIG. 1, third stiffening member 44 is secured within filler material or reinforcement member 28.

Figure 27B:
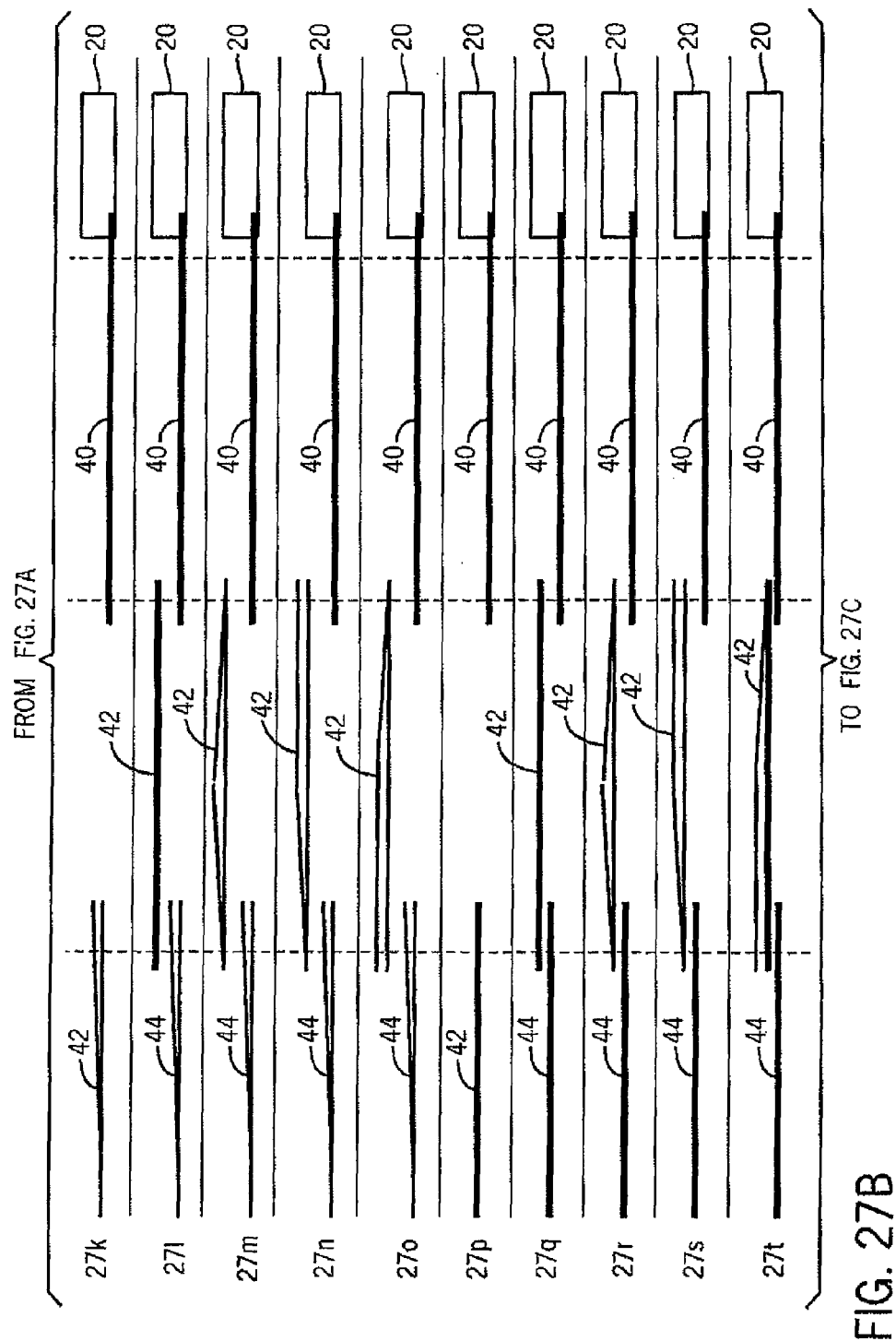
Figure 27D:
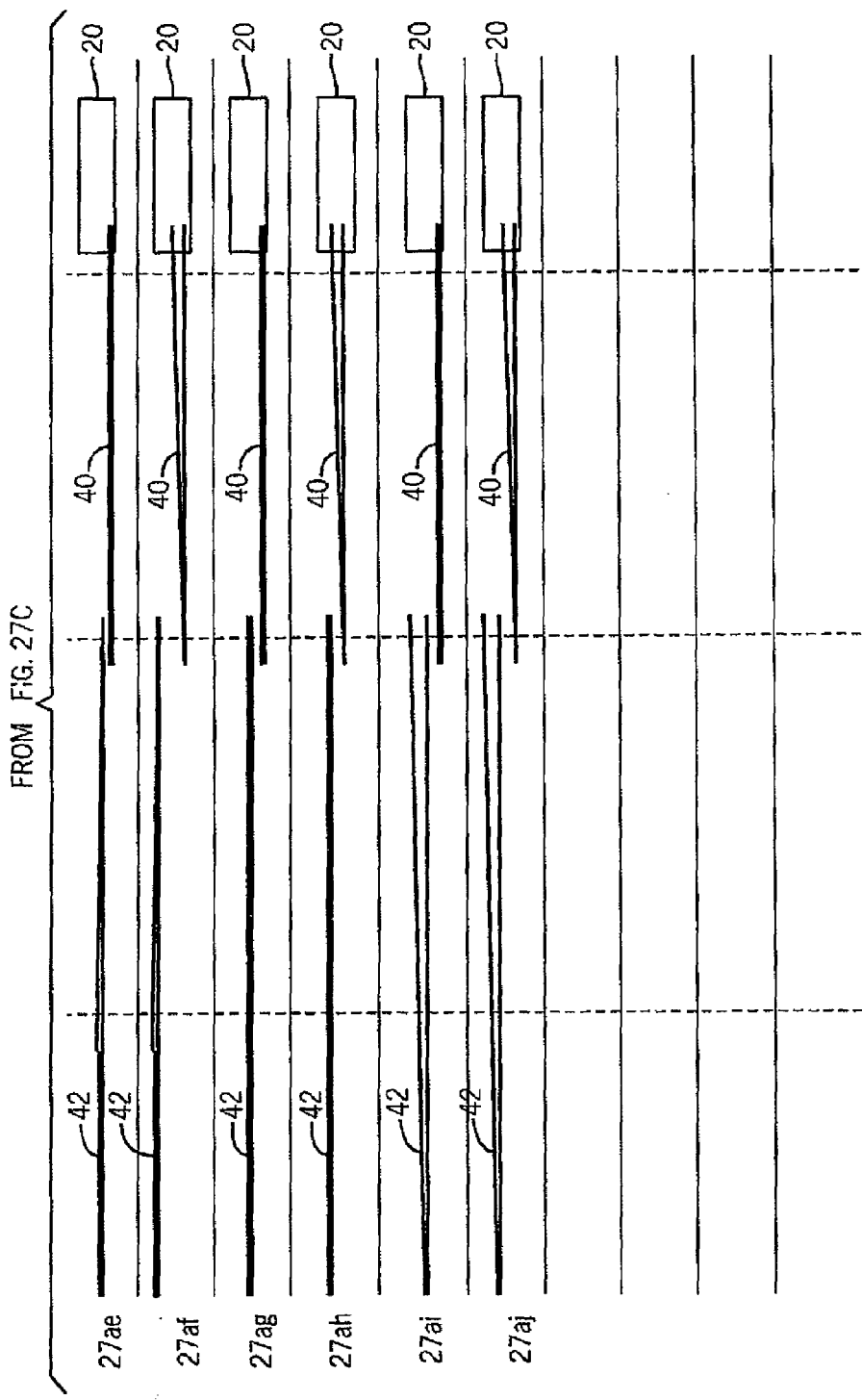

As embodied herein and depicted in FIG. 27A to 27D, the plurality of stiffening members can include at least first and second stiffening members arranged in a variety of ways along the elongate main body. In this manner and as illustrated in FIG. 27A to 27D, any of the first, second, or third stiffening members can include a distal taper, a proximal taper, or both a distal and proximal taper, depending upon the intended function and performance of the catheter. Additionally, any of the first, second, or third stiffening members can be configured without a taper. For example, embodiment number 27a of FIG. 27A depicts a first stiffening member having a tapered distal end and a second stiffening member having a tapered distal end, wherein the first and second stiffening members are in a non-overlapping arrangement. Embodiment 27b of FIG. 27A depicts a first stiffening member having a tapered distal end, a second stiffening member of uniform diameter and a third stiffening member having a tapered distal end. The remaining embodiments are evident from the drawings.

In yet another embodiment of the invention, the catheter can be configured to achieve a varied flexibility along a length thereof by including a tubular member having at least one stiffening member circumferentially disposed about the outer surface of the tubular member. As embodied herein and schematically depicted in FIGS. 30A and 30B, catheter 100' includes tubular member 30' comprising at least one stiffening member 40' including at least one cluster 46 including a plurality of helical turns or rotations 46a circumferentially disposed about the outer surface of tubular member 30' along a length of cluster 46.

Figure 30A:
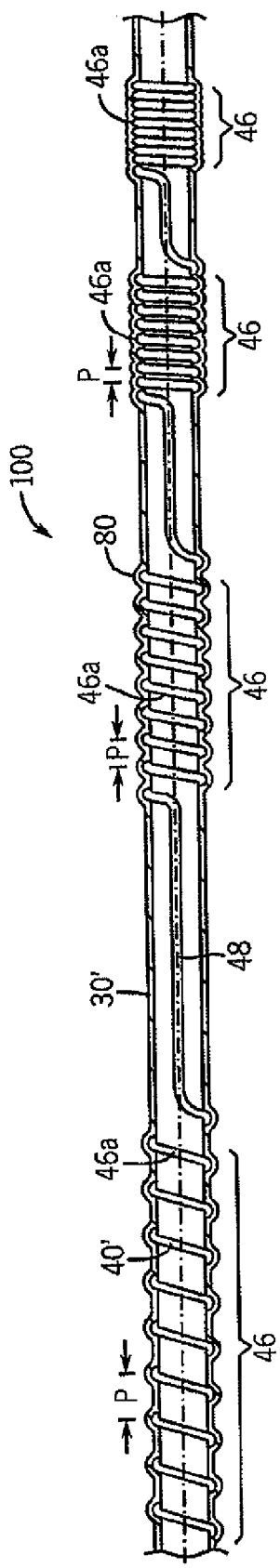
FIGS. 30A and 30B each schematically depict a tubular member having at least one stiffening member circumferentially disposed about the tubular member in accordance with the invention.
Figure 30B:
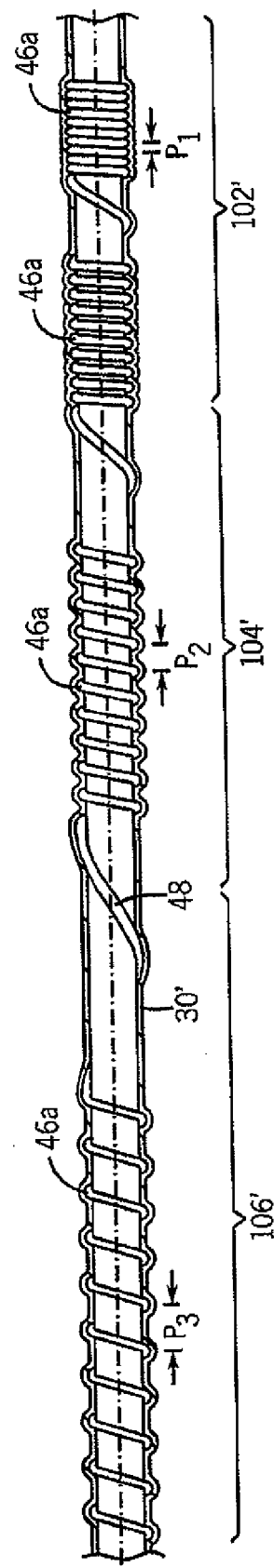

The plurality of helical turns have a predetermined pitch P. In this manner, the plurality of helical turns 46a can be configured to have a constant pitch along a length of the individual cluster 46, as shown in FIGS. 30A and 30B. Alternatively, the plurality of helical turns 46a can be configured to have a varied pitch along the length of the individual cluster (not shown).

In one embodiment, the at least one stiffening member includes a plurality of clusters 46 disposed along the length of the tubular member. The plurality of clusters can be configured to vary axial flexibility along a length of the tubular member. In this regard, the plurality of clusters includes a first cluster having a first flexibility disposed along a first length of the tubular member and a second cluster having a second flexibility disposed along a second length of the tubular member. The second flexibility can be greater than the first flexibility.

The variation in flexibility along the length of the tubular member can be achieved in many ways. For example and not limitation, the first cluster can be formed from a first material and the second cluster can be formed from a second material, the second material having greater flexibility than the first material. Accordingly, the length of the tubular member that is associated with the second cluster has a greater flexibility than the length of the tubular member associated with the first cluster. In this regard, the second cluster can be disposed along a distal portion of the tubular member and the first cluster can be disposed along the proximal portion of the tubular member. Accordingly, a tubular member having an increased flexibility distally along the length of the tubular member is defined.

Alternatively, the first cluster can include a first plurality of helical turns having a first pitch and the second cluster can include a second plurality of helical turns having a second pitch. The first pitch can be configured to be different than the second pitch. In this manner, the second pitch can be configured to have a longer pitch than the first pitch to define a cluster having greater flexibility along its length. The first cluster can be disposed along a length of the tubular member at which a greater stiffness is desired.

For the purpose of illustration, and as schematically depicted in FIG. 30B, tubular member 30' is configured to include proximal section 102', distal section 106' and intermediate section 104' disposed therebetween. In preferred embodiment, proximal section 102' includes a first cluster 46 including a first plurality of helical turns 46a having a first pitch P1 along the length of the first cluster, intermediate section 104' includes a second cluster 46 comprising a second plurality of helical turns 46a having a second pitch P2 along a length thereof, and distal section 106' includes a third cluster including a third plurality of helical turns 46a having a third pitch P3. As depicted, the first plurality of helical turns has the shortest pitch P1 and the third plurality of helical turns has the longest pitch. Further, the second plurality of helical turns has a second pitch P2 that is shorter than P3 but longer than P1. Accordingly, the first, second, and third plurality of helical turns and respective clusters are configured to define a tubular member having an increased flexibility distally along its length. To this end, a section of the tubular member having greater stiffness can be achieved by including a cluster comprising a plurality of helical turns having a shorter pitch along a length thereof and a section of the tubular member having greater flexibility can be achieved by including a cluster comprising a plurality of helical turns having a longer along a length thereof. Accordingly, a tubular member having variable stiffness or flexibility can be achieved by fluctuating the pitch of the plurality of helical turns between the plurality of clusters. Alternatively, the cluster can be configured to include a plurality of helical turns in which each successive helical turn has an increasing length in pitch.

In one embodiment, as depicted FIGS. 30A and 30B, the at least one stiffening member can include multiple stiffening members in which each cluster of the plurality of clusters is associated with an adjacent cluster by an interconnector 48. The interconnector 48 can be linear as depicted in FIG. 30A or non-linear as depicted in FIG. 30B. For example and not limitation, interconnector 48 can have a longitudinal, wavy sinusoidal configuration, or any other configuration as would be appreciated in the art. Alternatively, the least one stiffening member can comprise a unitary stiffening member configured to include at least one cluster including a plurality of helical turns.

In a further aspect of the invention, and as depicted in FIGS. 31A and 31B, a coating 80' can be applied on the surface of tubular member 30' having at least one stiffening member including a cluster of helical turns 46 to provide a tubular member having a smooth, continuous outer surface. In this manner, a polymeric, e.g., nylon, coating can be extruded or pultruded over the tubular member 30' and clusters of helical turns 46. However, a variety of other techniques for applying the coating can be utilized. For example and not limitation, the coating can be applied by techniques including powder coatings, spray coating, and dip coating, as understood in the art.

During the coating process, the thickness of the coating and the cross-sectional area of the tubular member can be varied, if desired, as for example by bump extrusion techniques during which vacuum pressure during the extrusion process is varied to define a varied degree of thickness or cross-sectional area along the wall of the tubular member. Accordingly, the varied thickness or varied cross-sectional area of the tubular member further defines a tubular member having variable stiffness along a length thereof.

In addition to or in lieu of coating 80', shrink wrap 80 can be applied over the tubular member and cluster of coil members, as depicted in FIG. 30A. For example and not limitation, the shrink wrap tubing 80' can be a polymer material such as PET. Moreover, the tubular member can further include a base polymeric layer disposed on the outer surface of the tubular member and under the at least one stiffening member, if desired.

At least one stiffening member can be formed from a metallic or non-metallic element. For example and not limitation, the stiffening member can be formed from a metal such as stainless steel. If desired, a non-metallic member can be used. For example, aramid, boron, glass fiber, carbon fiber, PEEK fibers and blends thereof. The non-metallic stiffening member can be woven, spun, braided, or coiled onto the tubular member. Further, the non-metallic stiffening member can be used when MRI compatibility is desired. For the purpose of illustration and not limitation, the tubular member having varied flexibility can be utilized as an outer or inner tubular shaft member of a catheter system or alternatively as a shaft section of a catheter system.

As embodied herein and depicted in FIGS. 1 and 7, and further in accordance with another aspect of the invention, catheter 100 includes at least one radiopaque marker band 36 affixed to a surface of first guidewire tube 32. As depicted in FIG. 7, marker band 36 includes a keyway in which the distal end region of third stiffening member 44 is slidingly disposed. Accordingly, third stiffening member 44 is slidingly engaged within marker band 36 to facilitate flexing, and can extend distal to marker band 36. Preferably, third stiffening member 44 further includes a stopper 50 or protrusion to increase pushability of catheter 100. Alternatively, the third stiffening member 44 can also terminate at the proximal end of inflatable member 114.

In an alternative embodiment, as schematically depicted in FIG. 2, catheter 100 can include only a first stiffening member 40 and a second stiffening member 42. As shown in FIG. 2, second stiffening member 42 extends proximally from marker band 36 to first stiffening member 40 and is in an overlapping configuration with a portion of first stiffening member 40. In an alternative embodiment, second stiffening member can be disposed distal of first stiffening member 40 and have a distal end region 42b terminate proximal to inflatable member 114. In this manner, second stiffening member 42 can be secured to the elongate main body of the catheter, for example by reinforcement member 26, 28. Alternatively, a single stiffening member can be provided. The single stiffening member can extend distally from proximal tubular member 20 to a desired location along the length of the main body. The single stiffening member can be secured at its proximal end or, more preferably, at an intermediate or distal location along its length.

Figure 29:
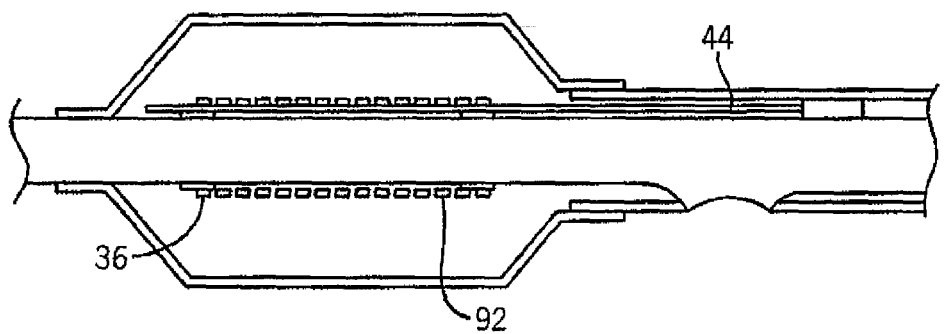
FIG. 29 depicts a catheter including at least one stiffening member and a support member in accordance with the invention.

In accordance with another embodiment of the invention, and as depicted in FIG. 22, the plurality of stiffening members includes a second stiffening member disposed distal of the first stiffening member such that a gap is defined between the first stiffening member and the second stiffening member. Further, a support member can be disposed between the first and second stiffening members, as shown in FIGS. 22 and 24. Alternatively, and as depicted in FIG. 29, the support member can be disposed in the distal section of the catheter. In one embodiment, the support member is in association with the inflatable member. The support member can be a tubular member, such as a polymeric or non-polymeric tube, a coil member or the like. In one embodiment, the support member is a carbon or carbon reinforced tubular member. Preferably, the carbon or carbon reinforced member is articulated.

In accordance with a further aspect of the invention, the plurality of stiffening members is configured to vary the axial flexibility along a length of the elongate main body of catheter 100. The plurality of stiffening members can be configured in a variety of ways to vary the axial flexibility along a length of the elongate main body. For example and not limitation, the material used to form each stiffening member can define the desired stiffness for each portion of the catheter body. In this manner, a variety of materials can be used for any of the plurality of stiffening members. For example and not limitation, the stiffening member can be formed of metals or metal alloys, such as stainless steel, nitinol, titanium, tantalum, Eligiloy, cobalt, chrome, nickel and any combination or alloy thereof. Alternatively, the stiffening members can be made of polymeric materials, such as polyamide, including polyamide copolymers, and polyimides, reinforced resin materials, including carbon fiber reinforced material, glass fiber reinforced material, and boron fiber reinforced material. As yet another alternative, the stiffening member can be formed of synthetic materials, such as carbon, Dacron® and/or Kevlar®, available from E.I. du Pont de Nemours and Company.

Each stiffening member can be formed of a different material or a material having a different stiffness to vary the flexibility along a length of the elongate main body of catheter 100. Alternatively, at least two stiffening members can be formed of the same material or materials having similar stiffness to define a length of the elongate main body having uniform stiffness. For the purpose of illustration and not limitation, first stiffening member can be formed of stainless steel 40, second stiffening member 42 can be formed of a carbon material or carbon reinforced material, and third stiffening member 44 can be formed of nitinol. In this regard, the region of the elongate main body corresponding to the nitinol stiffening member can have a greater axial flexibility that the areas corresponding to the stainless steel or carbon stiffening members. Accordingly, one variety of varying the flexibility along a length of the catheter includes the selection of material used to form each of the plurality of stiffening members.

Moreover, the stiffening member can be configured to have a varied flexibility along its length. For example, the stiffening member can be configured to include an increased cross dimensional area to reduce axial flexibility along its length, as depicted in FIG. 1, or can include a portion having a circular cross section and a portion including a semi-circular cross section as shown in FIG. 28, or can be otherwise changed in cross section, such as flattened, to change stiffness.

Alternatively, the stiffening member can be configured to include at least one cut 88 along its length. Preferably, the at least one cut includes a plurality of cuts along the length of the stiffening member. As embodied herein and depicted in FIGS. 19A and 19B, the at least one cut 88 can be a circumferential cut defining a circumferential groove 90. In this manner, the spacing between adjacent grooves can be varied along the length of the stiffening member to define an increasing or decreasing variation in flexibility along the length of the stiffening member. The flexibility of the stiffening member having at least one cut along its length can further be increased or decreased by tapering the outer diameter of the stiffening member, as shown in FIG. 19A.

Figure 25:
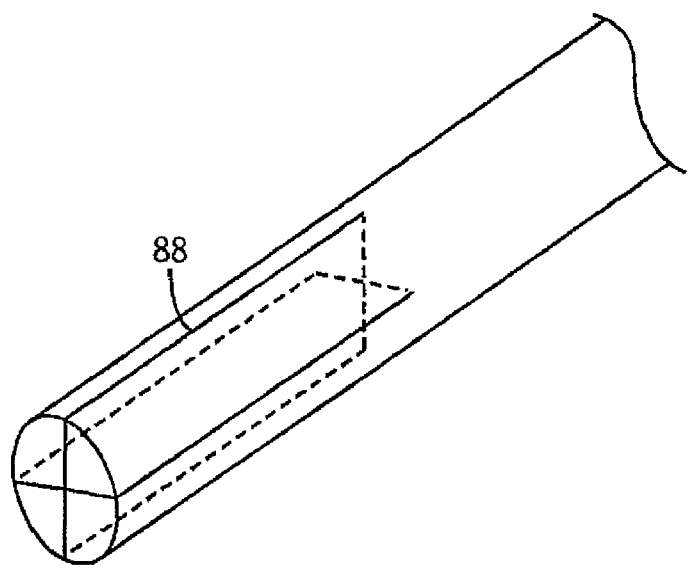
FIG. 25 is a schematic perspective view of a stiffening member having at least one longitudinal cut along a length thereof.
Figure 26:
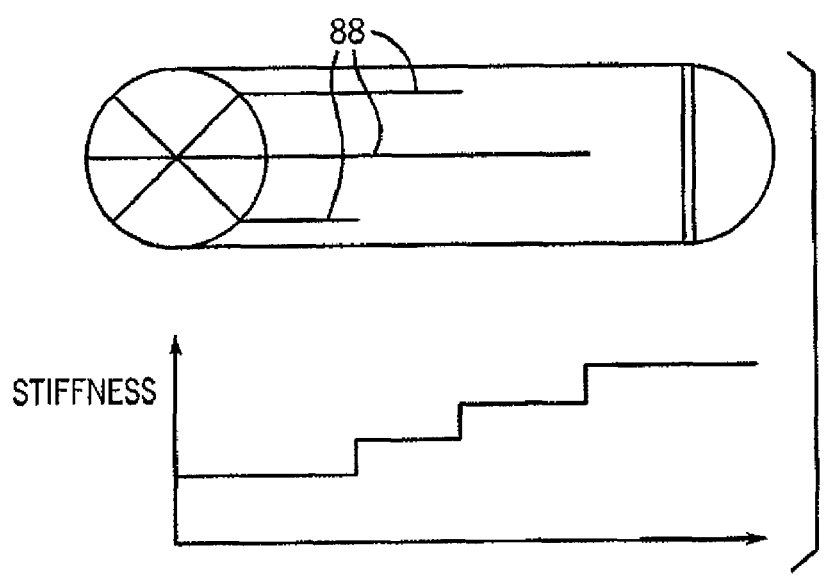
FIG. 26 is a schematic perspective view of a stiffening member having a plurality of longitudinal cuts, each cut having a different length, along a length of the stiffening member.

As yet another alternative, the cut 88 along the length of the stiffening member can include at least one longitudinal cut along its length, as depicted in FIG. 25. In this manner, the at least one longitudinal cut can include a plurality of longitudinal cuts in which at least a first longitudinal cut has a length different than a second longitudinal cut, as illustrated in FIG. 26, to vary the stiffness of the stiffening member.

Additionally, the length of each stiffening member will be dependent on the total number of stiffening members. For example and not limitation, if catheter 100 has three stiffening members, first stiffening member 40 can generally have a length of approximately 110 to 125 cm. Preferably, first stiffening member 40, as illustrated in FIGS. 1 and 2, terminates proximal to guidewire port 30a. Second stiffening member 42 generally has a length of about 5 to 15 cm. As depicted in FIG. 1, second stiffening member 42 preferably extends across guidewire port 30a. Third stiffening member 44 generally has a length of approximately 5 to 30 cm and preferably, greater than 10 cm. Preferably, third stiffening member extends proximally across gap 24d. If only first stiffening member 40 and second stiffening member 42 are used, at least one stiffening member would have a greater length.

As illustrated in FIGS. 18A to 18G at least one of the plurality of stiffening members can include a linear or, alternatively, an non-linear configuration. For example and not limitation, the first stiffening member can have a wavy configuration and the second stiffening member can have a linear configuration, as depicted in FIG. 18A. Alternatively, each of the first and second stiffening members can have a linear configuration as depicted in FIG. 18B and FIG. 18C. Alternatively, at least one stiffening member can be configured to include a linear portion and a non-linear portion as illustrated in FIGS. 18D and 18G. The non-linear configuration can include but not limited to a wavy configuration FIG. 18F or a helical configuration FIG. 18D.

Depending upon the materials of construction, and the intended use of the catheter, it can be beneficial to further reinforce the ports along the length of the catheter 100. Hence, in further accordance with the invention, and as schematically depicted in FIG. 1, catheter 100 can further include a first reinforcement member 26 and a second reinforcement member 28 disposed adjacent to proximal guidewire port 30a and gap 24d, respectively.

For the purpose of illustration and not limitation, first reinforcement member 26 is disposed in lumen 22c adjacent to proximal guidewire port 30a and defines reinforcement region 26a. Additionally, second reinforcement member 28 is disposed in inflation lumen 24c adjacent to distal guidewire port 24d, and defines reinforcement region 28a, as demonstrated in FIGS. 1 and 2. Each reinforcement member is melted upon formation of the corresponding joint, as previously described.

At least one of the first or second reinforcement members 26,28 can be in the form of a polymeric member formed of materials such as for example and not limitation, polyamide, PEEK, polyether ketone, polyketone. Preferably, at least one of first and second reinforcement members is a nylon tubular member.

As mentioned, first reinforcement member 26 and second reinforcement member 28 form first reinforcement region 26a and second reinforcement region 28a, respectively. For the purpose of illustration, a mandrel made of non-stick material, such as PTFE, and preferably having a desired shape corresponding to a lumen is slid within the lumen of the tubular reinforcement member. Additionally, if desired, a corresponding stiffening member can also be inserted in the lumen of the tubular reinforcement member. For example, second stiffening member 42 can be disposed in the reinforcement member 26, and third stiffening member 44 can be inserted in the lumen of second tubular reinforcement member 28. A shrink tube can be placed over the welding zone and the assembly is then heated. The application of heat will act to melt the polymer material, and cause the molten polymer of the first tubular reinforcement member 26 to form a first reinforcing region 26a, and cause the molten polymer of the second tubular reinforcement member 28 to form second reinforcing region 28a.

As illustrated in FIG. 3, after fusing or melting first reinforcement member 26, for example by applying heat, the mandrel is removed, and inflation lumen 24c is defined (by the mandrel), and the molten polymer which corresponds to first reinforcement region 26a causes second stiffening member 42 to become embedded within reinforcing region 26a. Similarly, as depicted in FIG. 6, inflation lumen 24c is defined and a portion of third stiffening member 44 is embedded within reinforcement region 28a, which is defined by the molten polymer of second reinforcement member 28. Advantageously, each of reinforcement region 26a and 28a can act to reinforce or support a length of elongate main body of catheter 100, and also to secure stiffening member 42 and stiffening member 44, respectively. Further, the reinforcement region can act to seal the inflation lumen at the guidewire ports.

In further accordance with the invention, a sheath is provided for a balloon catheter. In one embodiment, the balloon catheter is a rapid exchange catheter having a proximal port in the sidewall of the catheter body. As shown and depicted in FIGS. 35A and 35B sheath 200 preferably includes a proximal section 202 and a distal section 204. In one preferred embodiment, the proximal sheath section 202 is stationary and is configured to cover the proximal port disposed in the sidewall of the rapid exchange catheter and the distal sheath section 204 is retractable and is configured to cover at least a balloon portion of the catheter, which may include a stent.

For the purpose of illustration and not limitation, in one embodiment, the proximal sheath section 202 extends from the proximal section of the catheter body to a point between the proximal side port and the balloon. In operation, the distal sheath section 204 is retracted proximally and telescopically slides over a surface of the proximal sheath section 202 to expose the balloon (and stent if provided). In this manner, the distal sheath section 204 can be operatively attached to the pull wire or actuator (FIG. 34, 220), for example, with a radiopaque pull collar.

Figure 33:
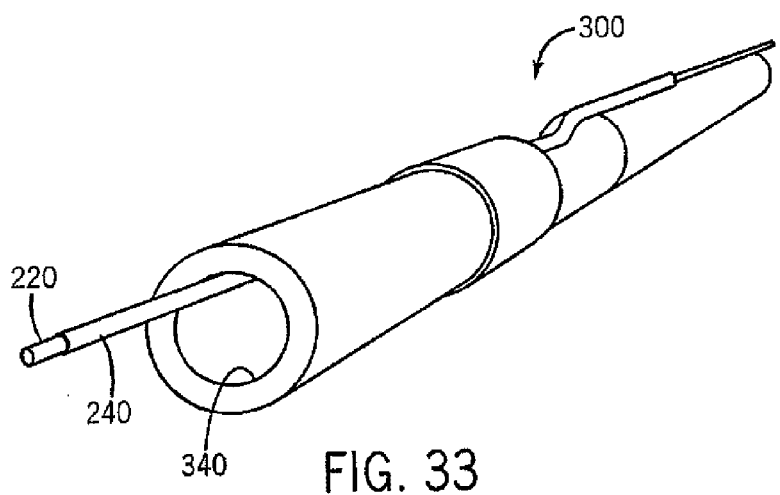
FIG. 33 is schematically depicts a tubular member of a catheter having an actuator secured in the lumen of the tubular member in accordance with the invention.
Figure 34:
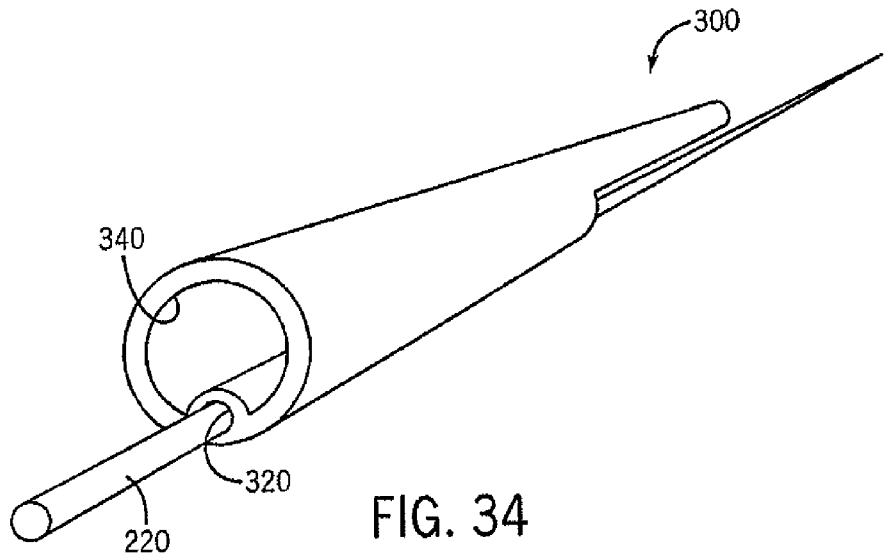
FIG. 34 schematically depicts a tubular member of a catheter having a lumen configured to receive an actuator in accordance with the invention.
Figures 35A, 35B:
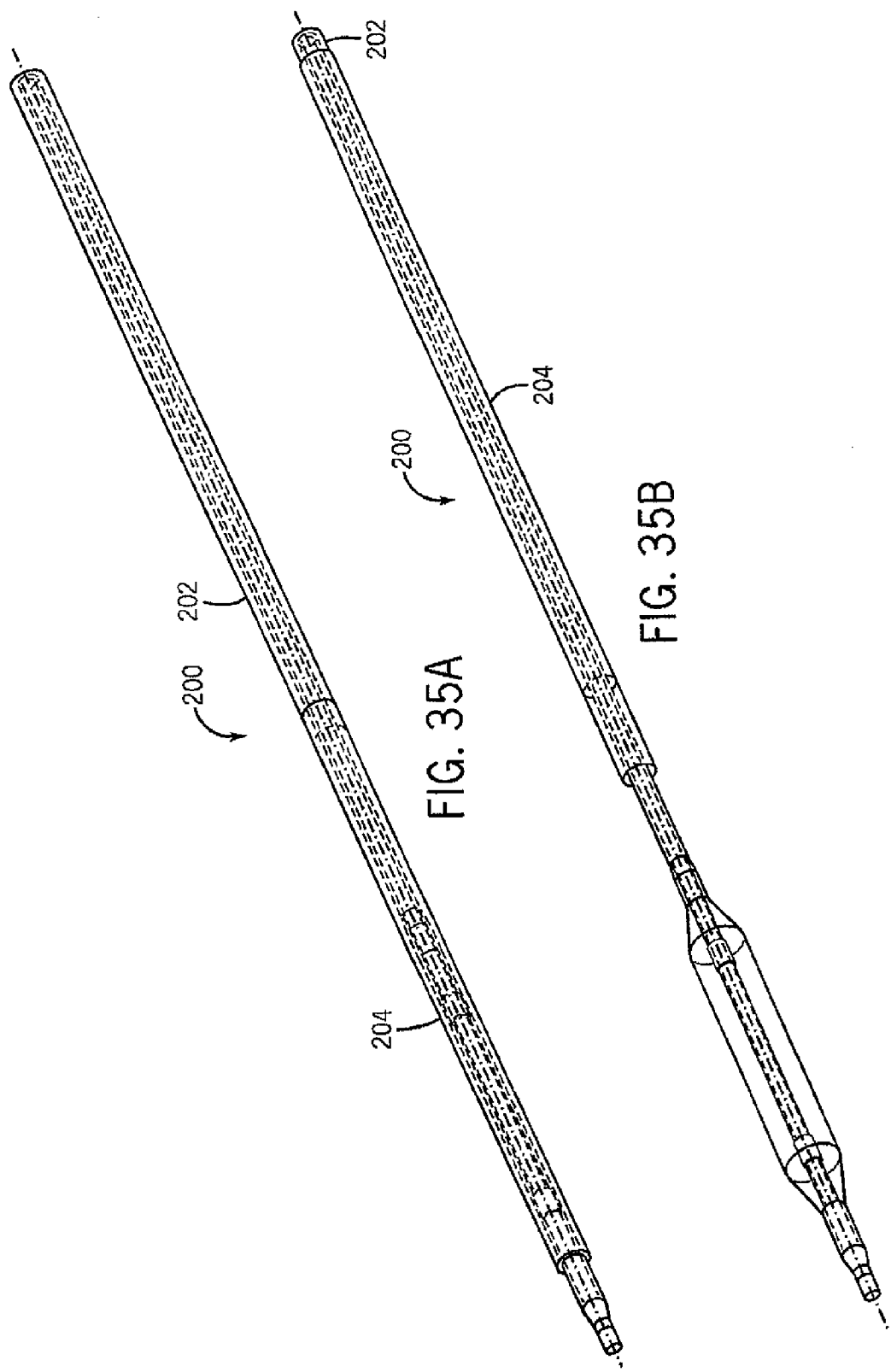
FIGS. 35A and 35B schematically depict an embodiment of a sheath in accordance with the invention.

For the purpose of illustration and not limitation, and as depicted in FIGS. 33 and 34, the actuator, e.g., pull wire 220, can be disposed in the lumen of the proximal section of the catheter body 300. For example, the pull wire 220 can be disposed in a dedicated lumen 320 disposed within the lumen of the inflation shaft 340 of the catheter 300, as depicted in FIG. 34. Alternatively, as depicted in FIG. 33, the actuator 220 can be disposed within a polymeric microtube 240 that is secured to the inner surface of the lumen of the inflation shaft 340 of catheter 300. Further, the microtube 240 can be free floating in the lumen of the inflation shaft 340, i.e., not secured to the lumen. In any arrangement, the pull wire extends coaxially along the lumen of the catheter. In a preferred embodiment, the actuator 220 exits the lumen of the catheter at a point distal of proximal tubular member and extends distally along the exterior and outer surface of the catheter body, as depicted in FIGS. 33 and 34. The proximal sheath section 202 is disposed on the catheter body such that the sheath covers at least a portion of the proximal section of the catheter, the proximal port in the sidewall of the catheter body and at least a portion of the actuator along the exterior of the catheter body (not shown). Accordingly, the sheath can be configured such that a stationary sheath section provides a protective cover for the proximal side port of the catheter and the actuator while further allows uncompromised movement of the actuator. The proximal sheath section 202, preferably, is secured to the catheter body at or near the proximal port to ensure lack of movement of the sheath section. Additionally, the retractable distal sheath section 204 provides a protective cover for the balloon section of the catheter body.

As depicted in FIGS. 36A and 36B, the sheath can be configured to further include a bellowed section 206 disposed between the proximal sheath section 202 and the distal sheath section 204. In this manner, the sheath can be formed from a unitary tubular member or alternatively can be made from multiple tubular members secured together, for example, by welding or adhesively bonding the proximal sheath section 202, bellowed sheath section 206 and the distal sheath section 204. The compressible bellowed section 206 provides variable sheath length. In this manner, the bellowed section is operatively attached to a pull wire or actuator. During retraction, the bellowed section compresses and causes the distal sheath section to move proximally thereby exposing the stent and the balloon.

A variety of types of medical devices are suitable for delivery by the catheter of the present invention. For purpose of example and not limitation, a medical device can be provided, for example, in the form of a balloon-expandable stent (not shown). Such devices are generally well known in the art. However, the catheter of the present invention is not limited to the delivery of balloon expandable stents. Other devices may also be used. For example, stent-grafts, bifurcation systems, coils, filters, heart valve repair devices, and embolic protection devices may be delivered within a patient's vasculature using catheter 100 of the present invention. Other devices such as a prosthesis retrieval mechanism, antennae for intravascular MRI, or visual or ultrasonic imaging devices can also be delivered or used with catheter at a predetermined location in a patient's luminal systems. Moreover, combinations of medical devices and/or beneficial agents or pharmaceutically active agents can also be delivered using the device of the present invention. For example, multiple stents or a combination of stents and embolic protection devices and/or beneficial agents can be delivered using catheter of the present invention, mounted on separate inflatable members (not shown). Further, the catheter of the invention may include two or more balloons or one balloon with a plurality of inflatable sections. Accordingly, in the event that a catheter is required with more than one inflation lumen, for example for the introduction of contrast media or inflation of a second balloon, the proximal section of elongate main body can further include a second proximal tubular member coaxially disposed about proximal tubular member 30 or hypotube. Preferably, the second proximal member is a polymeric material, e.g., nylon or HDPE, however, the second proximal member may be formed of a hypotube.

Although reference has been made to a catheter having an inflatable member 114 at its distal body section, a variety of other structures for delivering to or use within a luminal system can be provided. For example, if desired, it is also possible to deliver self-expanding medical devices on a catheter of the invention. In accordance with this aspect of the invention, a medical device in the form of a self-expanding prosthesis, such as a self-expanding stent, can be provided. If a self-expanding medical device is to be delivered using the catheter of the invention, it may be necessary to provide a restraint device to restrain expansion of the medical device, and permit deployment at the appropriate time by a physician. Such a restraint device can take the form of a retractable sheath having a proximal end, a distal end, an inner surface and an outer surface. Sheath can be withdrawn proximally so as to deploy the medical device by actuating an actuator (not shown). The actuator can be a simple push-pull actuator, a gear mechanism, or a hydraulic actuator, spring loaded actuator, or pneumatic actuator. Alternatively, the actuator can be electrically or chemically driven artificial muscle, which is based on contractile alloys or polymers. For example and not limitation, the contractile alloys can be Flexinol, available from Dynalloy Inc. Costa Mesa, Calif., or polyacrylonitrile- polypyrrole- or polyvinylalcohol-fibers.

The actuator can be attached to sheath directly at proximal end of sheath, or may be attached by a pull wire. Alternatively, the actuator can be attached to a unravel-able system, such as a knitted member. Such actuators are provided in, for example, U.S. Pat. No. 6,425,898 to Wilson, U.S. Pat. No. 5,906,619 to Olson, U.S. Pat. No. 5,772,669 to Vrba and U.S. Pat. No. 6,527,789 to Lau et al., each of which is incorporated by reference herein in its entirety.

A variety of other restraint devices can additionally or alternatively be used. For example, restraint bands (not shown) could alternatively be used that are retracted proximally by a pull wire attached to an actuator. Similarly, restraint device can take the form of a frangible envelope (not shown) with a pull wire embedded within the wall of the envelope. Self expanding medical device can accordingly be deployed by actuating actuator, which pulls back on the pull wire, splitting open the frangible envelope, resulting in deployment of the self-expanding device. Other possible actuators (e.g., thermal actuation, wire restraints, balloon-ruptured restraints and the like) are also possible and within the scope of the invention.

In accordance with another aspect of the invention and as previously described in conjunction with certain aspects of the invention, a method of performing a medical procedure is provided. The method includes providing a catheter as described herein, disposing a guidewire within a lumen of a patient, and inserting the guidewire through at least one of the first guidewire lumen and the second guidewire lumen of the catheter.

The method in accordance with the invention can also include providing and inflating an inflatable member in a lumen of a patient, retracting the guidewire until a distal extremity of the guidewire is proximal to the proximal guidewire port 30a of the intermediate section 104 of the catheter, and allowing blood to perfuse through the first guidewire lumen of the distal body portion.

The methods and systems of the present invention, as described above and shown in the drawings, provide for a catheter with superior properties including superior flexibility and pushability. It will be apparent to those skilled in the art that various modifications and variations can be made in the device and method of the present invention without departing from the spirit or scope of the invention. Thus, it is intended that the present invention include modifications and variations that are within the scope of the appended claims and their equivalents.

What is claimed is:

1. A catheter comprising:
   an elongate main body including at least a proximal section and a distal section; and
   a plurality of stiffening members disposed along a length of the elongate main body, the plurality of stiffening members including a first stiffening member having a proximal end and a distal end, and a second stiffening member having a proximal end and a distal end, the distal end of the first stiffening member disposed in an overlapping spaced relationship relative to the proximal end of the second stiffening member;
   wherein the distal end of the first stiffening member and the proximal end of the second stiffening member each has a reduced cross-section defined therein.

2. The catheter of claim 1, wherein the first stiffening member is secured to the elongate main body and is disposed along the proximal portion of the elongate main body.

3. The catheter of claim 1 wherein the catheter further includes an adapter secured to the proximal portion of the elongate body, the first stiffening member secured to the adapter at least one location.

4. The catheter of claim 1, wherein the catheter further includes a support member, at least one of the first stiffening member and the second stiffening member secured to the support member.

5. The catheter of claim 1 wherein at least one of the proximal end and the distal end of the first stiffening member is unsecured to the elongate main body.

6. The catheter of claim 1, wherein the second stiffening member is secured to at least one location along the elongate main body and is disposed along at least the distal portion of the elongate main body.

7. The catheter of claim 1, wherein at least one of the plurality of stiffening members is secured to an inner surface of the elongate main body.

8. The catheter of claim 7, wherein the at least one of the plurality of stiffening members is secured to the inner surface with filler material.

9. The catheter of claim 1, wherein the catheter further includes an engagement member secured to a surface of the elongate main body such that a longitudinal space is defined between the engagement member and the surface of the elongate main body, at least one stiffening member having a length engaged in the longitudinal space.

10. The catheter of claim 1, wherein the plurality of stiffening members are configured to vary axial flexibility along a length of the elongate main body.

11. The catheter of claim 10, wherein the first stiffening member is disposed along a first length of the elongate main body, the second stiffening member is disposed along a second length of the elongate main body distal of the first length, the second stiffening member having a greater axial flexibility than the first stiffening member.

12. The catheter of claim 1, wherein at least one of the first stiffening member and the second stiffening member is formed from a material including metal, metal alloy, polymer, composite, carbon, and carbon reinforced material.

13. The catheter of claim 1, wherein the first stiffening member is formed from a first material, the second stiffening member is formed from a second material, the first material being different than the second material.

14. The catheter of claim 1, wherein at least one of the plurality of stiffening members has an outer diameter along a length thereof, the at least one of the plurality of stiffening members further including at least one cut defined along the length thereof.

15. The catheter of claim 14, including a plurality of cuts, each of the plurality cuts defines a circumferential groove spaced along the length of the stiffening member.

16. The catheter of claim 15, wherein the spacing between adjacent grooves is varied along the length of the stiffening member to define a stiffening member having a varied flexibility along the length thereof.

17. The catheter of claim 14, wherein the cut extends longitudinally along at least a portion of the outer diameter to reduce stiffness of the stiffening member.

18. The catheter of claim 1, wherein at least a portion of the at least one of the plurality of stiffening members includes a non-linear configuration.

19. The catheter of claim 18, wherein the non-linear configuration is wavy.

20. The catheter of claim 18, wherein the non-linear configuration is helical.

21. The catheter of claim 1, wherein the plurality of stiffening members further includes a third stiffening member disposed in an overlapping spaced relationship relative the second stiffening member, the third stiffening member having a proximal end and a distal end.

22. The catheter of claim 21, wherein the third stiffening member is formed from a third material, the third material having a flexibility different than the first material forming the first stiffening member and the second material forming the second stiffening member.

23. The catheter of claim 1, wherein the reduced cross-section of the first stiffening member is a distal taper and the reduced cross-section of the second stiffening member is a proximal taper.

24. The catheter of claim 1, wherein at least one of the stiffening members is made of a non-metallic material.

25. The catheter of claim 14, wherein the reduced cross-section of at least one of the first stiffening member or the second stiffening member is defined by the at least one cut therein.

* * * * *